United States Patent [19]
Villalobos et al.

[11] Patent Number: 6,093,733
[45] Date of Patent: Jul. 25, 2000

[54] MUSCARINIC RECEPTOR AGONISTS

[76] Inventors: Anabella Villalobos, 47 Greencliff Dr., Niantic, Conn. 06357; Daniel Yohannes, 600 Meridian St. Ext., Groton, Conn. 06340; Jolanta Nowakowski, 10 Otter Brook Dr., Old Saybrook, Conn. 06475; Dane R. Liston, 68 Main St., Noank, Conn. 06340

[21] Appl. No.: 08/848,359

[22] Filed: Apr. 30, 1997

Related U.S. Application Data

[60] Provisional application No. 60/016,494, Apr. 30, 1996.
[51] Int. Cl.$^7$ .................... A61K 31/445; C07D 265/00; C07D 211/28
[52] U.S. Cl. .................... 514/331; 514/183; 514/212; 514/228.8; 514/231.2; 514/318; 514/428; 540/450; 540/609; 544/63; 544/105; 546/193; 546/231; 548/586
[58] Field of Search .................... 540/450, 609; 544/63, 105; 546/193, 231; 548/586; 514/183, 212, 228.8, 231.2, 318, 331, 428

[56] References Cited

U.S. PATENT DOCUMENTS 5,268,373  12/1993  Breslin et al. .................... 514/231.8

OTHER PUBLICATIONS

Goerdeler et al. "Acyl carbodiimides II . . . " CA 87:184175, 1977.

US Congress "The biology of Mental disorders", Library of Congress, p 45–47, 55, 1992.

*Primary Examiner*—Ceila Chang
*Attorney, Agent, or Firm*—Raymond M. Speer, Esq.

[57] ABSTRACT

This invention relates to a novel class of partial or full muscarinic receptor agonists intermediates for their preparation, and pharmaceutical compositions and methods of use for the treatment or prevention of diseases the treatment or prevention of which is mediated by muscarinic receptor agonism.

20 Claims, No Drawings

MUSCARINIC RECEPTOR AGONISTS

This application claims benefit of provisional application Ser. No. 60/016,474, filed Apr. 30, 1996.

BACKGROUND OF THE INVENTION

This invention relates to a novel class of partial or full muscarinic receptor agonists, intermediates for their preparation, and pharmaceutical compositions and methods of use for the treatment or prevention of diseases the treatment or prevention of which is mediated by muscarinic receptor agonism. Some compounds described exhibit muscarinic antagonist activity or mixed agonist/antagonist activity and thereby are useful for treatment or prevention of diseases or syndromes characterized by excessive cholinergic activity.

Muscarinic receptors are pre- and post-synaptic receptors in the cholinergic neurotransmitter system. Disruption of the cholinergic neurotransmitter system has been implicated in age related central nervous system (CNS) dysfunction. Muscarinic receptor agonists are believed, by those of ordinary skill in the art, to be useful in treating or preventing age related CNS dysfunction, such as cognitive decline and Alzheimer's disease that results from disruption of the cholinergic neurotransmitter system.

Specific evidence for the role of the cholinergic neurotransmitter system in age related CNS dysfunction has been reported by Bartus, R. T. et al., in *The Cholinergic Hypothesis of Geriatric Memory Dysfunction.* Science, 217, 408–417 (1982). The authors hypothesize that a disruption of the central cholinergic system may be responsible for age-related CNS impairment. (See also, Perry, E. K., *The Cholinergic Hypothesis—Ten Years On,* Br. Med. Bull., 42, 63–69 (1986)).

Further evidence for the support of the cholinergic hypothesis has been offered by Sims, et al., *Presynaptic Cholinergic Dysfunction in Patients with Dementia,* J. Neurochem., 40, 503–509 (1983). These authors have demonstrated that the acetylcholine neurotransmitter system is implicated in age-related CNS disorders by showing that activity of cholinergic markers such as choline acetyltransferase is markedly reduced in the brains of patients with Alzheimer's disease (AD) in comparison to age-matched controls.

Additionally, it has been shown that cholinergic neurons which originate at the nucleus basalis of Meynert and project into the hippocampus and cortex show extensive degeneration in Alzheimer's Disease. See Vogel et al. *Cell Loss and Shrinkage in the Nucleus Basalis Meynert Complex in Alzheimer's Disease.* Neurobiol. Aging, 11, 3–13 (1990); and Whitehouse et al., *Alzheimer's Disease and Senile Dermentia: Loss of Neurons in the Basal Forebrain,* Science, 215, 1237–1239 (1982).

Furthermore, it has been shown that muscarinic antagonists such as scopolamine can induce cognitive impairments in normal subjects similar to that of normal aging. See Sitaram, et al., *Human Serial Learning: Enhancement with Arecoline and Choline and Impairment with Scopolamine.* Science, 201, 274–276 (1978); and Drachman D. A. *Memory and Cognitive Function in Man: Does the Cholinergic System have a Specific Role?* Neurology, 27, 783–790 (1977).

Based on the above research, it is commonly believed that potentiation of central cholinergic action will be a useful treatment of conditions exhibiting cognitive decline.

One strategy to enhance cholinergic neurotransmission has been to mimic the action of acetylcholine at the muscarinic receptors with appropriate agonists. There are three pharmacologically defined receptors ($M_1$–$M_3$) and recently five human receptors ($m_1$–$m_5$) have been cloned (Bonner, et al., *Identification of a Family of Muscarinic Acetylcholine Receptor Genes,* Science, 237, 527–532 (1987); and Bonner, T. I., *The Molecular Basis of Muscarinic Receptor Diversity,* T.I.N.S., 12, 148–151 (1989). Due to the lack of highly selective ligands for each subtype, it has not been possible to unambiguously establish the biological role of the individual receptors. However, it is believed that central $m_1$ receptors mediate cognition and the $m_2$–$m_5$ subtypes are responsible for side effects (salivation, lacrimation, diarrhea). Immunoprecipitation studies have shown a preponderance of the human $m_1$ receptor in the cortex and hippocampus, areas of the brain involved in memory and learning. Ideally, a selective $m_1$ agonist would be a desirable agent for treating the cognitive decline associated with neurodegenerative disorders.

In addition to age related cognitive decline, muscarinic agents are also known to be effective in the treatment of psychotic conditions, pain, sleep disorders, depression, seasonal affective disorder and tardive dyskinesias.

Muscarinic agents are known to influence schizophrenia and other psychotic conditions and the atypical antipsychotic clozapine possesses selective $m_4$ agonist activity which is important for its clinical profile (Zorn et al., *Clozapine Is A Potent And Selective Muscarinic M4 Receptor Agonist,* Eu. J. Pharmacol., 269, R1–R2, (1994). Clozapine is also used to treat the tardive dyskinesias that frequently arise following treatment with typical antipsychotics.

Muscarinic agonists are also known to produce robust analgesia, comparable to that produced by opiate analgesics. (P. Hartvig et al., *Cholinergic mechanisms in pain and analgesia,* Trends Pharmacol. Sci., 9, 75–79, (1989)).

Muscarinic antagonists are also believed to be effective agents in treating diseases or syndromes characterized by overactivation of muscarinic receptors. Cholinergic regulation of sleep, particularly the REM phase, indicates that the muscarinic agents will be useful in treating sleep disorders such as insomnia and somnolence (D. Reimann et al., *Cholinergic Neurotransmission. REM Sleep And Depression,* J. Psychosom. Res. 38, 15–25, (1994)). Muscarinic systems also modulate psychiatric depression (K. Davis et al., *Induction of Depression With Oxotremorine In Patients With Alzheimer's Disease,* Am. J. Psychiatry, 144, 468–471, (1987)), including seasonal affective disorder (S. C. Dilsaver et al., *Bright Artificial Light Subsensitizes a Central Muscarinic Mechanism,* Life Sci., 41, 2607–2614, (1987)).

Muscarinic antagonists are also useful in the treatment of diseases associated with altered motility or tone of smooth muscle such as irritable bowel syndrome, urinary incontinence, diverticular disease, oesophageal achalasia and chronic obstructive airways disease.

U.S. Pat. No. 4,211,867, issued Jul. 8, 1980, refers to nitrogen heterocyclic carboximidamide derivatives. The compounds are stated to possess hypoglycemic activity.

U.S. Pat. No. 4,414,211, issued Nov. 8, 1983, refers to heterocyclic derivatives of guanidine. The compounds are stated to possess hypoglycemic activity.

SUMMARY OF THE INVENTION

The present invention relates to compounds of the formula

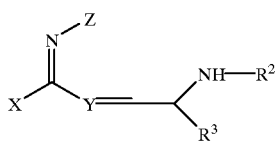

I wherein X is $NR^4R^5$, $(C_1-C_{10})$alkyl or $(C_3-C_{10})$cycloalkyl, wherein said $(C_3-C_{10})$cycloalkyl may optionally be substituted with from one to three substituents, preferably one or two substituents, independently selected from the group consisting of —$OR^6$, $(C_1-C_4)$alkyl, oxo and a ketal of the formula —O—$(CH_2)_n$—O—;

n is an integer from one to three;
m is an integer from one to three;
p is an integer from one to three;
Y is N or CH;
Z is $NR^7R^8$, $(C_3-C_{10})$cycloalkyl, $(C_1-C_{10})$alkyl, pyridyl or phenyl; wherein said phenyl or $(C_3-C_{10})$cycloalkyl may optionally be substituted with from one to three substituents, preferably one or two substituents, independently selected from the group consisting of $(C_1-C_6)$alkyl, halo, hydroxy, $(C_1-C_6)$alkoxy, amino, $(C_1-C_6)$-alkylamino, di$(C_1-C_6)$-alkylamino and trifluoromethoxy;

$R^2$ is phenyl optionally substituted with from one to three substituents, preferably one or two substituents, independently selected from the group consisting of $(C_1-C_6)$alkyl, halo, hydroxy, $(C_1-C_5)$alkoxy, amino, $(C_1-C_6)$-alkylamino, di$(C_1-C_6)$-alkylamino, —$CF_3$, —CN, —$COR^6$, $NHCOR^6$ and trifluoromethoxy;

$R^3$ is phenyl optionally substituted with from one to three substituents, preferably one or two substituents, independently selected from the group consisting of $(C_1-C_6)$alkyl, halo, hydroxy, $(C_1-C_6)$alkoxy, amino, $(C_1-C_6)$-alkylamino, di$(C_1-C_6)$-alkylamino and trifluoromethoxy;

$R^4$ and $R^5$ are independently $(C_1-C_{10})$alkyl or $R^4$ and $R^5$ taken together with the nitrogen atom to which they are attached form a (five to nine)-membered saturated heterocyclic ring in which one of the ring atoms may optionally be replaced with a heteroatom selected from the group consisting of nitrogen, oxygen and sulfur, wherein said (five to nine)-membered saturated heterocyclic ring may optionally be substituted with from one to three substituents, preferably one or two substituents, independently selected from the group consisting of —$OR^6$, $(C_1-C_4)$alkyl, oxo and a ketal of the formula —O—$(CH_2)_m$—O—; with the proviso that said substituted heterocycles may not be substituted next to a heteroatom by hydroxy or a ketal;

$R^6$ is hydrogen or $(C_1-C_6)$alkyl; and
$R^7$ and $R^8$ are independently $(C_1-C_{10})$alkyl or $R^7$ and $R^8$ taken together with the nitrogen atom to which they are attached form a (five to seven)-membered saturated heterocyclic ring in which one of the ring atoms may optionally be replaced with a heteroatom selected from the group consisting of nitrogen, oxygen and sulfur, wherein said (five to seven)-membered saturated heterocyclic ring may optionally be substituted with from one to three substituents, preferably one or two substituents, independently selected from the group consisting of —$OR^6$, $(C_1-C_4)$alkyl, oxo and a ketal of the formula —O—$(CH_2)_p$—O—; with the proviso that said substituted heterocycles may not be substituted in the two position by hydroxy or a ketal;

and the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The above heterocyclic ring systems described as X and Z include, but are not limited to, pyrrolidine, piperidine, thiomorpholine, hexamethyleneimine, heptamethyleneimine, tetrahydrooxazine, tetrahydrothiazine, morpholine, tetrahydrooxazine, thiomorpholine, tetrahydrodiazine, piperazine, oxazolidine, thiazolidine, pyrazolidine, tetrahydrodiazepine, tetrahydrooxazepine, tetrahydrothiazepine, perhydrodiazocine, perhydrodiazonine, perhydroazonine, and perhydrothiazonine.

The compounds of the invention include all stereoisomers and all optical isomers of the formula I (e., R and S enantiomers) and their racemic and diastereomeric mixtures. The compounds of the invention include all tautomers and geometric isomers.

Preferred compounds of the invention are compounds of formula I wherein:

Z is pyridyl or phenyl optionally substituted with from one to three substituents independently selected from the group consisting of $(C_1-C_6)$alkyl, halo, hydroxy, $(C_1-C_6)$alkoxy, amino, $(C_1-C_6)$alkylamino, di$(C_1-C_6)$-alkylamino and trifluoroalkoxy;

X is $NR^4R^5$ and $R^4$ and $R^5$ are taken together with the nitrogen atom to which they are attached to form an optionally substituted five to nine membered saturated heterocyclic ring selected from piperidine, pyrrolidine, thiomorpholine, hexamethylenimine, morpholine, thiazolidine and 1,2-tetrahydrooxazine;

$R^2$ is phenyl optionally substituted with halo, hydroxy or methoxy; and $R^3$ is phenyl substituted with one or two substituents independently selected from the group consisting of $(C_1-C_6)$ alkyl, halo, hydroxy, $(C_1-C_6)$alkoxy, amino, $(C_1-C_6)$ alkylamino di$(C_1-C_6)$-alkylamino and trifluoroalkoxy.

More preferred compounds of the invention are compounds of formula I wherein:

X is an optionally substituted heterocycle selected from piperidine and 1,2-tetrahydrooxazine;

$R^2$ is phenyl optionally substituted with halo, hydroxy or methoxy; and $R^3$ is phenyl substituted with one or two substituents independently selected from $(C_1-C_6)$alkyl, halo, hydroxy, $(C_1-C_6)$alkoxy, amino, $(C_1-C_6)$alkylamino di$(C_1-C_6)$-alkylamino and trifluoroalkoxy.

More preferred compounds of the invention are those wherein:

$R^2$ is phenyl substituted in the 4-position of the phenyl ring with fluoro or methoxy; and $R^3$ is phenyl substituted with two substituents independently selected from $(C_1-C_6)$alkyl, halo, hydroxy, $(C_1-C_6)$ alkoxy, amino, di$(C_1-C_6)$-alkylamino and trifluoroalkoxy.

Most preferred compounds of the invention are those of the formula I wherein X is piperidine substituted in the two position with $(C_1-C_4)$alkyl and $R^3$ is 2,6-dimethylphenyl.

Specific examples of preferred compounds of formula I include the following:

N-[(2,6-dimethyl-phenyl)-(4-fluoro-phenylimino)-methyl]-2-methyl-N'-phenyl-piperidine-1-carboxamidine;

N-(4-fluoro-phenyl)-2-methyl-N'-[(2-methyl-piperidin-1-yl)-phenylimino-methyl]-benzamidine;

N-(4-fluoro-phenyl)-2-methyl-N'-([1,2]oxazinan-2-yl-phenylimino-methyl)-benzamidine;

N-(4-methoxy-phenyl)-2,6-dimethyl-N'-[(2-methyl-piperidin-1-yl)-phenylimino-methyl]-benzamidine;

N-(4-fluoro-phenyl)-2-methyl-N'-[(2-methyl-piperidin-1-yl)-o-tolylimino-methyl]-benzamidine;

N-(4-fluoro-phenyl)-N'-[(4-hydroxy-2-methyl-piperidin-1-yl)-phenylimino-methyl]-2,6-dimethyl-benzamidine;

N-(4-fluoro-phenyl)-N'-[(4-hydroxy-2-methyl-piperidin-1-yl)-phenylimino-methyl]-2,6-dimethyl-benzamidine;

N-(4-fluoro-phenyl)-2,6-dimethyl-N'-[(2-methyl-piperidin-1-yl)-(pyridin-3-ylimino)-methyl]-benzamidine;

(3-phenylimino-3-[2-methyl]piperidin-1-yl-1-o-tolyl-propenyl)-(4-fluoro-phenyl)-amine;

(3-phenylimino-3-[1,2]oxazinan-2-yl-1-o-tolyl-propenyl)-(4fluoro-phenyl)-amine;

(3-phenylimino-3-[1,2]oxazinan-2-yl-1-o-tolyl-propenyl)-(4-methoxy-phenyl)-amine;

N-[cyclopropylimino-(2-methyl-piperidin-1-yl)-methyl]-N'-(4fluoro-phenyl)-2,6-dimethyl-benzamidine;

N-(cyclopropylimino-[1,2]oxazinan-2-yl-methyl)-N'-(4-fluoro-phenyl)-2,6-dimethyl-benzamidine;

N-[cyclopropylimino-(1-methyl-cyclohexyl)-methyl]-N'-(4-fluoro-phenyl)-2-methyl-benzamidine; and (3-cyclopropylimino-3-[1,2]oxazinan-2-yl-1-o-tolyl-propenyl)-(4-fluoro-phenyl)-amine.

Other compounds of the invention include:

N-phenyl-N'-(phenylimino-pyrrolidin-1-yl-methyl)-benzamidine;

N-phenyl-N'-(phenylimino-piperidin-1-yl-methyl)-benzamidine;

N-phenyl-N'-(phenylimino-thiomorpholin4-yl-methyl)-benzamidine;

N, N-diethyl-N'-phenyl-N"-(phenyl-phenylamino-methylene)-guanidine;

N-(4-fluoro-phenyl)-N'-(phenylimino-pyrrolidin-1-yl-methyl)-benzamidine;

N-(4-methoxy-phenyl)-N'-(phenylimino-pyrrolidin-1-yl-methyl)-benzamidine;

N-(4-chloro-phenyl)-N'-(phenylimino-pyrrolidin-1-yl-methyl)-benzamidine;

N-(azepan-1-yl-phenylimino-methyl)-N'-phenyl-benzamidine;

N-(azepan-1-yl-phenylimino-methyl)-N'-(4-methoxy-phenyl)-benzamidine;

N-(azepan-1-yl-phenylimino-methyl)-N'-(4-fluoro-phenyl)-benzamidine;

2-methyl-N-phenyl-N'-(phenylimino-pyrrolidin-1-yl-methyl)-benzamidine;

N-[(4-methyl-piperidin-1-yl)-phenylimino-methyl]-N'-phenyl-benzamidine;

N-(azocan-1-yl-phenylimino-methyl)-N'-phenyl-benzamidine;

N-[(2-methyl-piperidin-1-yl)-phenylimino-methyl]-N'-phenyl-benzamidine;

N-[(3-methyl-piperidin-1-yl)-phenylimino-methyl]-N-N'-phenyl-benzamidine;

N-[(4-hydroxy-piperidin-1-yl)-phenylimino-methyl]-2-methyl-N'-phenyl-benzamidine;

N-[(4-fluoro-phenylimino)-pyrrolidin-1-yl-methyl]-N'-phenyl-benzamidine;

N-(4-fluoro-phenyl)-N'-[(4hydroxy-piperidin-1-yl)-phenylimino-methyl]-2-methyl-benzamidine;

N-[(2-fluoro-phenylimino)-pyrrolidin-1-yl-methyl]-N'-phenyl-benzamidine;

N-[(4-fluoro-phenylimino)-(4-hydroxy-piperidin-1-yl)-methyl]-2-methyl-N'-phenyl-benzamidine;

2-chloro-N-phenyl-N'-(phenylimino-pyrrolidin-1-yl-methyl)-benzamidine;

N-[(2,6-dimethyl-phenyl)-phenylimino-methyl]-N'-phenyl-pyrrolidine-1-carboxamidine;

N-[(2-methyl-piperidin-1-yl)-phenylimino-methyl]-N'-phenyl-benzamidine;

N-[(2-methyl-piperidin-1-yl)-phenylimino-methyl]-N'-phenyl-benzamidine;

N-(azepan-1-yl-phenylimino-methyl)-N'-(4fluoro-phenyl)-2-methyl-benzamidine;

N-(4-fluoro-phenyl)-N'-[(2-fluoro-phenylimino)-(4-hydroxy-piperidin-1-yl)-methyl]-2-methyl-benzamidine;

N-[(2-chloro-phenyl)-(4-fluoro-phenylimino)-methyl]-2-methyl-N'-phenyl-piperidine-1-carboxamidine;

N-[(3-hydroxy-piperidin-1-yl)-phenylimino-methyl]-N'-phenyl-benzamidine;

N-[(2-fluoro-phenyl)-phenylimino-methyl]-N'-phenyl-pyrrolidine-1-carboxamidine;

N-(4-fluoro-phenyl)-2-methyl-N'-[(2-methyl-piperidin-1-yl)-(pyridin-4-ylimino)-methyl]-benzamidine;

N-([1,2]oxazinan-2-yl-phenylimino-methyl)-N'-phenyl-benzamidine;

N-[(1,4-dioxa-8-aza-spiro[4.5]dec-8-yl)-phenylimino-methyl]-N'-phenyl-benzamidine;

N-(4-fluoro-phenyl)-2-methyl-N'-[(1-methyl-cyclohexyl)-phenylimino-methyl]-benzamidine;

N-(4-fluoro-phenyl)-N'-[(4-fluoro-phenylimino)-(2-methyl-piperidin-1-yl)-methyl]-2,6-dimethyl-benzamidine;

2,6-difluoro-N-(4-fluoro-phenyl)-N'-[(2-methyl-piperidin-1-yl)-phenylimino-methyl]-benzamidine;

2,6-dichloro-N-(4-fluoro-phenyl)-N'-[(2-methyl-piperidin-1-yl)-phenylimino-methyl]-benzamidine;

N-[(4-chloro-phenylimino)-(2-methyl-piperidin-1-yl)-methyl]-N'-(4-fluoro-phenyl)-2,6-dimethyl-benzamidine;

N-(adamantan-1-yl-phenylimino-methyl)-N'-(4-fluoro-phenyl)-2-methyl-benzamidine;

N-[(2,6-dimethyl-piperidin-1-yl)-phenylimino-methyl]-N'-(4-fluoro-phenyl)-2,6-dimethyl-benzamidine;

N-[azepan-1-yl-(4-fluoro-phenylimino)-methyl]-N'-(4-fluoro-phenyl)-2,6-dimethyl-benzamidine;

N-(4-fluoro-phenyl)-N'-[(4-fluoro-phenylimino)-[1,2] oxazinan-2-yl-methyl]-2,6-dimethyl-benzamidine:

2,6-difluoro-N-(4-fluoro-phenyl)-N'-[(4-fluoro-phenylimino)-(2-methyl-piperidin-1-yl)-methyl]-benzamidine;

N-[(2,6-dimethyl-piperidin-1-yl)-(4-fluoro-phenylimino)-methyl]-2,6-difluoro-N'-(4-fluoro-phenyl)-benzamidine;

N-(azepan-1-yl-phenylimino-methyl)-N'-(4-fluoro-phenyl)-2,6-dimethyl-benzamidine;

N-[(2,6-dimethyl-piperidin-1-yl)-(4-fluoro-phenylimino)-methyl]-N'-(4-fluoro-phenyl)-2,6-dimethyl-benzamidine;

N-[(2,6-dimethyl-piperidin-1-yl)-phenylimino-methyl]-2,6-difluoro-N'-(4-fluoro-phenyl)-benzamidine;

N-(azepan-1-yl-phenylimino-methyl)-2,6-difluoro-N'-(4-fluoro-phenyl)-benzamidine;

N-[azepan-1-yl-(4-fluoro-phenylimino)-methyl]-2,6-difluoro-N'-(4-fluoro-phenyl)-benzamidine;

N-[(2-ethyl-piperidin-1-yl)-phenylimino-methyl]-N'-(4-fluoro-phenyl)-2,6- dimethyl-benzamidine;

N-[(2,6-dimethyl-piperidin-1-yl)-phenylimino-methyl]-N'-(4-fluoro-phenyl)-2,6-dimethyl-benzamidine;

N-(4-methoxy-phenyl)-2-methyl-N'-[(2-methyl-piperidin-1-yl)-phenylimino-methyl]-benzamidine;
N-(4-fluoro-phenyl)-2,6-dimethyl-N'-([1,2]oxazinan-2-yl-phenylimino-methyl)-benzamidine;
N-(4-fluoro-phenyl)-N'-[(3-hydroxy-piperidin-1-yl)-phenylimino-methyl]-2,6-dimethyl-benzamidine;
N-(4-fluoro-phenyl)-2,6-dimethyl-N'-[(4-oxo-piperidin-1-yl)-phenylimino-methyl]-benzamidine;
N-[(4-amino-phenylimino)-(2-methyl-piperidin-1-yl)-methyl]-N'-(4-fluoro-phenyl)-2,6-dimethyl-benzamidine;
N-(4-fluoro-phenyl)-2,6-dimethyl-N'-[(2-methyl-4-oxo-piperidin-1-yl)-phenylimino-methyl]-benzamidine;
N-(4-fluoro-phenyl)-N'-[(3-hydroxy-piperidin-1-yl)-phenylimino-methyl]-2-methyl-benzamidine;
N-(4-methoxy-phenyl)-2,6-dimethyl-N'-([1,2]oxazinan-2-yl-phenylimino-methyl)-benzamidine;
N-(4-hydroxy-phenyl)-2,6-dimethyl-N'-[(2-methyl-piperidin-1-yl)-phenylimino-methyl]-benzamidine;
N-(azepan-1-yl-phenylimino-methyl)-N'-(4-methoxy-phenyl)-2,6-dimethyl-benzamidine;
N-(4-fluoro-phenyl)-2-methyl-N'-[(4-oxo-piperidin-1-yl)-phenylimino-methyl]-benzamidine;
N-(4-fluoro-phenyl)-2-methyl-N'-[(2-methyl-4-oxo-piperidin-1-yl)-phenylimino-methyl]-benzamidine;
N-[(3-amino-phenylimino)-(2-methyl-piperidin-1-yl)-methyl]-N'-(4-fluoro-phenyl)-2,6-dimethyl-benzamidine;
N-(4-fluoro-phenyl)-N'-[(4-hydroxy-piperidin-1-yl)-phenylimino-methyl]-2,6-dimethyl-benzamidine;
N-(4-fluoro-phenyl)-N'-[(4-hydroxy-2-methyl-piperidin-1-yl)-phenylimino-methyl]-2,6-dimethyl-benzamidine;
N-[(3-amino-phenylimino)-(2-methyl-piperidin-1-yl)-methyl]-2,6-dimethyl-N'-(4-trifluoromethoxy-phenyl)-benzamidine;
2,6-dimethyl-N-[(2-methyl-piperidin-1-yl)-phenylimino-methyl]-N'-(4-trifluoromethoxy-phenyl)-benzamidine;
N-(4-fluoro-phenyl)-2,6-dimethyl-N'-(morpholin-4-yl-phenylimino-methyl)-benzamidine;
N-(4-fluoro-phenyl)-2,6-dimethyl-N'- [(2-methyl-piperidin-1-yl)-m-tolylimino-methyl]-benzamidine;
N-(4-fluoro-phenyl)-N'-[(3-fluoro-phenylimino)-(2-methyl-piperidin-1-yl)-methyl]-2,6-dimethyl-benzamidine;
N-[(2-chloro-phenylimino)-(2-methyl-piperidin-1-yl)-methyl]-N'-(4-fluoro-phenyl)-2-methyl-benzamidine;
N-(4-fluoro-phenyl)-N'-[(2-methoxy-phenylimino)-(2-methyl-piperidin-1-yl)-methyl]-2-methyl-benzamidine;
N-(4-fluoro-phenyl)-N'-[(3-methoxy-phenylimino)-(2-methyl-piperidin-1-yl)-methyl]-2,6-dimethyl-benzamidine;
N-(4-fluoro-phenyl)-2,6-dimethyl-N'-[(2-methyl-piperidin-1-yl)-o-tolylimino-methyl]-benzamidine;
N-[(2-chloro-phenylimino)-(2-methyl-piperidin-1-yl)-methyl]-N'-(4-fluoro-phenyl)-2,6-dimethyl-benzamidine;
(3-phenylimino-3-pyrrolidin-1-yl-1-phenyl-propenyl)-phenylamine;
(3-phenylimino-3-thiazolidin-3-yl-1-phenyl-propenyl)-phenylamine;
(3-phenylimino-3-[2-methyl]piperidin-1-yl-1-[2-chlorophenyl]-propenyl)-(4-fluorophenyl)-amine;
(3-[4-fluorophenylimino]-3-[2-methyl]piperidin-1-yl-1-o-tolyl-propenyl)-(4-fluoro-phenyl)-amine;
(3-phenylimino-3-[2-methyl]piperidin-1-yl-phenyl-propenyl)-phenylamine;
(3-cyclohexylimino-3-[1,2]oxazinan-2-yl-1-o-tolyl-propenyl)-(4-fluoro-phenyl)-amine;
N-[cyclohexylimino-(1-methyl-cyclohexyl)-methyl]-N'-(4-fluoro-phenyl)-2-methyl-benzamidine;
N-[cyclohexylimino-(2-methyl-piperidin-1-yl)-methyl]-N'-(4fluoro-phenyl)-2,6-dimethyl-benzamidine;
N-[cyclohexylimino-(2-methyl-piperidin-1-yl)-methyl]-N'-(4-fluoro-phenyl)-2-methyl-benzamidine;
N-[sec-butylimino-(2-methyl-piperidin-1-yl)-methyl]-N'-(4-fluoro-phenyl)-2,6-dimethyl-benzamidine;
N-(4-fluoro-phenyl)-N'-[isopropylimino-(2-methyl-piperidin-1-yl)-methyl]-2,6-dimethyl-benzamidine;
[3-cyclohexylimino-3-(2-methyl-piperidin-1-yl)-1-o-tolyl-propenyl]-(4-fluoro-phenyl)-amine;
N-(adamantan-1-yl-cyclohexylimino-methyl)-N'-(4-fluoro-phenyl)-2-methyl-benzamidine;
N-[cyclobutylimino-(2-methyl-piperidin-1-yl)-methyl]-N'-(4-fluoro-phenyl)-2,6-dimethyl-benzamidine;
N-[cyclopropylimino-(2-methyl-piperidin-1-yl)-methyl]-N'-(4-fluoro-phenyl)-2-methyl-benzamidine;
N-[cyclopropylimino-(2-methyl-piperidin-1-yl)-methyl]-N'-(4-methoxy-phenyl)-2,6-dimethyl-benzamidine;
N-[cyclopropylmethylimino-(2-methyl-piperidin-1-yl)-methyl]-N'-(4-fluoro-phenyl)-2,6-dimethyl-benzamidine;
(3-cyclopropylimino-3-[1,2]oxazinan-2-yl-1-phenyl-propenyl)-(4fluoro-phenyl)-amine;
N-[allylimino-(2-methyl-piperidin-1-yl)-methyl]-N'-(4-fluoro-phenyl)-2,6-dimethyl-benzamidine;
N-(4-fluoro-phenyl)-2,6-dimethyl-N'-[(2-methyl-piperidin-1-yl)-(morpholin-4-ylimino)-methyl]-benzamidine;
N-(4-fluoro-phenyl)-2,6-dimethyl-N'-[(2-methyl-piperidin-1-yl)-(piperidin-1-ylimino)-methyl]-benzamidine; and
N-(4-fluoro-phenyl )-2,6-dimethyl-N'-[(2-methyl-cyclopropylimino)-(2-methyl-piperidin-1-yl)-methyl]-benzamidine.

The present invention also relates to a pharmaceutical composition for treating or preventing a disease or condition, the treatment or prevention of which can be effected or facilitated by enhancing cholinergic neurotransmission in a mammal, comprising a muscarinic receptor binding effective amount of a compound of formula I or a pharmaceutically acceptable salt thereof and a pharmaceutically acceptable carrier.

The present invention also relates to a method of treating or preventing a disease or condition, the treatment or prevention of which can be effected or facilitated by enhancing cholinergic neurotransmission in a mammal, comprising administering to said mammal a muscarinic receptor binding effective amount of a compound of formula I or a pharmaceutically acceptable salt thereof.

The present invention also relates to a pharmaceutical composition for treating or preventing a disease or condition, the treatment or prevention of which can be effected or facilitated by enhancing cholinergic neurotransmission in a mammal, comprising administering to said mammal an amount of a compound of formula I or a pharmaceutically acceptable salt thereof that is effective in treating or preventing such condition.

The present invention also relates to a method of treating or preventing a disease or condition, the treatment or prevention of which can be effected or facilitated by enhancing cholinergic neurotransmission in a mammal, comprising administering to said mammal an amount of a compound of formula I or a pharmaceutically acceptable salt thereof that is effective in treating or preventing such condition.

The present invention also relates to a method of treating, preventing or diagnosing a disease or condition selected from the group consisting of psychotic disorders, pain, sleep disorders, depression, Alzheimer's disease, tardive dyskinesia, Picks disease, Huntington's chorea, Friederich's ataxia, Gilles de la Tourette's disease, Down's Syndrome, attention-deficit disorder, multi-infarct dementia, and age-related cognitive decline (ARCD) in a mammal, comprising administering to a mammal, including a human, in need of such treatment, prevention or diagnosis an amount of a compound according to claim 1 effective in treating, preventing or diagnosing such condition.

The present invention also relates to a pharmaceutical composition for treating, preventing or diagnosing a disease or condition selected from the group consisting of psychotic disorders, pain, sleep disorders, depression, Alzheimer's disease, tardive dyskinesia, Picks disease, Huntington's chorea, Friederich's ataxia, Gilles de la Tourette's disease, Down's syndrome, attention-deficit disorder, multi-infarct dementia, and age-related cognitive decline (ARCD) in a mammal, including a human, comprising an amount of a compound according to claim 1 effective in treating, preventing or diagnosing such condition and a pharmaceutically acceptable carrier.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine, bromine, and iodine.

The compounds of formula I contain olefin or imine bonds and therefore may exist in cis or trans forms. This invention relates to all isomers and all stereoisomers of compounds of the formula I, and mixtures thereof.

The phrase "a ketal of the formula —O—$(CH_2)_p$—O—" when used herein refers to a spiro group that can be added to a ketone in the presence of an acid catalyst and a glycol.

"Enhancing cholinergic neurotransmission," when used herein, refers to improving the neuronal process whereby acetylcholine is released by a presynaptic cell upon excitation and crosses the synapse to stimulate or inhibit the post-synaptic cell. The compounds of the invention also function by increasing the cholinergic response by mimicking the action of acetylcholine at the cholinergic receptors.

When X is $NR^4R^5$ and $R^4$ and $R^5$ together form an optionally substituted (three to nine)-membered heterocyclic ring and when Z is $NR^7R^8$ and $R^7$ and $R^8$ together form an optionally substituted (five to seven)-membered saturated heterocyclic ring then one of skill in the art will appreciate that the following rings are meant to be included within these definitions.

5 MEMBERED HETEROCYCLES

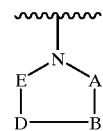

| Name | A | B | D | E | Reference |
|---|---|---|---|---|---|
| pyrrolidine | C | C | C | C | U.S. Pat. No. 3,095,423; U.S. Pat. No. 3,109,005. |
| isoxazolidine | O | C | C | C | DE 2,339,185; Synthesis, 5, 426–428 (1982); U.S. Pat. No. 2,762,815; Arzneim. Forsch., 27, 766–770 (1977). |
| 1,3 oxazolidin-3-yl | C | O | C | C | Parravicini et al., Farmaco Ed. Sci., 31, 49–57 (1976); Kricheldorf, Makromol. Chem., 176, 57–74 (1975). |
| isothiazolidine | S | C | C | C | EP 626,377. |
| 1,3 thiazolidin-3-yl | C | S | C | C | Larice et al., Bull. Soc. Chim, Fr., 2053–2056 (1971); Barbry et al., J. Chem. Soc. Perkin Trans. 2, 1, 133–140 (1990); Hansen et al., Tetrahedron Lett., 35, 38, 6971–6974 (1994). |
| 1,2 pyrazolidin-2-yl | N | C | C | C | Stetter et al., Chem. Ber., 98, 3228–3235 (1965); Kornett, J. Pharm. Sci., 58, 724–727 (1969); Oppolzer, Tetrahedron Lett., 35, 3091–3094 (1970). |
| 1,3 pyrazolidin-1-yl | C | N | C | C | Freter et al., Justus Liebigs Ann. Chem., 607, 174–184(1957). |

6 MEMBERED HETEROCYCLES

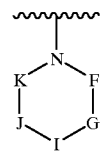

| Name | F | G | I | K | L | Reference |
|---|---|---|---|---|---|---|
| piperidine | C | C | C | C | C | U.S. Pat. No. 5,364,943 |
| 1,2 tetrahydro oxazin-2-yl | O | C | C | C | C | Khomutov et al., Bull. Acad. Sci. USSR Div. Chem. Sci., 1006–1008 (1962). |
| 1,3 tetrahydro oxazin-3-yl | C | O | C | C | C | Kalyuskii et al., J. Org. Chem., 25, 10, 1989–1991 (1989); Linde et al., Arzneim. Forsch., 28, 937–939 (1978). |

6 MEMBERED HETEROCYCLES

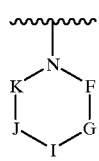

| Name | F | G | I | K | L | Reference |
|---|---|---|---|---|---|---|
| morpholine | C | C | O | C | C | J.A.C.S., 47, 2966 (1925); J.A.C.S., 58, 2338 (1936). |
| 1,2 tetrahydro thiazin-2-yl | S | C | C | C | C | Kharasch, J. Org. Chem., 28, 1901–1902 (1963). |
| 1,3 tetrahydro thiazin-3-yl | C | S | C | C | C | Bergmann et al., Recl. Trav. Chim. Pays-Bas., 78, 327–330 (1959). |
| thiomorpholino | C | C | S | C | C | Davies, J. Chem. Soc., 117, 298–306 (1920). |
| 1,2 tetrahydro diazin-2-yl | N | C | C | C | C | Baranger et al., Bull. Soc. Chim. Fr., 704, 708 (1957); Selenin et al., Khim. Geterotsikl. Soedin., 530, 533 (1968); Testa, Farmaco Ed. Sci., 26, 950–954 (1971). |
| 1,3 tetrahydro diazin-1-yl | C | N | C | C | C | Skaric et al., Croat. Chem. Acta., 38, 1–4 (1966). |
| piperazine | C | C | N | C | C | J.A.C.S., 51, 3074 (1929); U.S. Pat. No. 3,037,023. |

7 MEMBERED MONOCYCLIC HETEROCYCLES

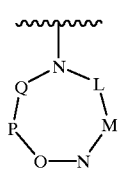

| Name | L | M | N | O | P | Q | Reference |
|---|---|---|---|---|---|---|---|
| 1,2 perhydro oxazepin-2-yl | O | C | C | C | C | C | Amiaiky et al., Synthesis, 5, 426–428, (1982). |
| 1,3 perhydro oxazepin-3-yl | C | O | C | C | C | C | Bergmann et al., Recl. Trav. Chim. Pays-Bas., 78, 327–330 (1959). |
| 1,4 perhydro oxazepin-4-yl | C | C | O | C | C | C | Farberow et al., Zh. Obshch. Khim., 25, 133–135 (1955). |
| 1,2 perhydro thiazepin-2-yl | C | S | C | C | C | C | Grob et al., Helv. Chim. Acta., 57, 2562–2571 (1974). |
| 1,2 perhydro thiazepin-2-yl | C | C | S | C | C | C | Black, J. Chem. Soc. C, 1708–1710 (1966); Can. J. Chem., 49, 2612–2616 (1971); J. Org. Chem., 46, 7, 1239–1243 (1981); and J. Org. Chem., 25, 1953–1956 (1960); DE 1,195,317. |
| 1,2 perhydro diazepin-1-yl | N | C | C | C | C | C | Rutjes et al., Tetrahedron Lett., 32, 45, 6629–6632 (1991); and Fritschi et al., Helv. Chem. Acta., 74, 8, 2024–2034 (1991). |
| 1,3 perhydro diazepin-1-yl | C | N | C | C | C | C | Gunawardane, Indian J. Chem. Sect. A, 27, 5, 380–386 (1988). |

7 MEMBERED MONOCYCLIC HETEROCYCLES

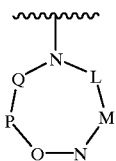

| Name | L | M | N | O | P | Q | Reference |
|---|---|---|---|---|---|---|---|
| 1,4 perhydro diazepin-1-yl | C | C | N | C | C | C | Poppelsdorf et al., J. Org. Chem., 26, 131–134 (1961); Ziegler et al., J. Med. Chem., 33, 1, 142–146 (1990); and Dickerman et al., J. Org. Chem., 14, 530–536 (1949). |
| hexamethyl eneimin-1-yl | C | C | C | C | C | C | Benson et al., J. Amer. Chem. Soc., 70, 2115–2117 (1948); Wang et al., J. Amer. Chem. Soc., 114, 1, 248–255 (1992); U.S. Pat. No. 1,253,558; and U.S. Pat. No. 1,253,456. |

8 MEMBERED HETEROCYCLES

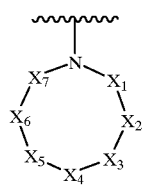

| Name | $X_1$ | $X_2$ | $X_3$ | $X_4$ | $X_5$ | $X_6$ | $X_7$ | $X_8$ | Reference |
|---|---|---|---|---|---|---|---|---|---|
| heptamethyl eneimine | C | C | C | C | C | C | C | C | Guttieri et al., J. Org. Chem., 49, 16, 2875–2880 (1984). |
| 1,2 perhydro diazocine | N | C | C | C | C | C | C | C | J. Org. Chem., 37, 1851 (1972); and J.A.C.S., 92, 4922–4925 (1970). |
| 1,4 perhydro diazocine | C | C | N | C | C | C | C | C | Majchrzak et al., Acta Pol. Pharm., 32, 145 (1975). |
| 1,5 perhydro diazocine | C | C | C | N | C | C | C | C | Alder et al., J. Chem. Soc. Perkin Trans. 2, 3, 411–418 (1984). |

9 MEMBERED HETEROCYCLES

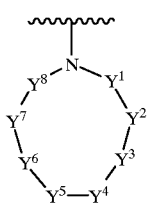

| Name | $Y^1$ | $Y^2$ | $Y^3$ | $Y^4$ | $Y^5$ | $Y^6$ | $Y^7$ | $Y^8$ | Reference |
|---|---|---|---|---|---|---|---|---|---|
| octahydro azonine | C | C | C | C | C | C | C | C | Blicke, J. Amer. Chem. Soc., 76, 2317–2319 (1954); and U.S. Pat. No. 2,051,575. |
| 1,5 perhydro thiazonine | C | C | C | S | C | C | C | C | Wise et al., J. Med. Chem., 17, 11, 1232–1234 (1974). |
| 1,4 perhydro diazonine | C | C | N | C | C | C | C | C | Alder et al., Tetrahedron Lett., 23, 40, 4181–4184 (1982). |
| 1,5 perhydro diazonine | C | C | C | N | C | C | C | C | Croker et al., Tetrahedron Lett., 24, 14, 1559–1560 (1983). |

DETAILED DESCRIPTION OF THE INVENTION

The compounds of formula I can be prepared according to the methods of Schemes 1–5. In the reaction Schemes and discussion that follow, A, m, n, p, $R^2$, $R^3$, $R^4$, $R^5$, $R^6$, $R^7R^8$, X, Y and Z, unless otherwise indicated, are as defined above for formula I.

SCHEME 1
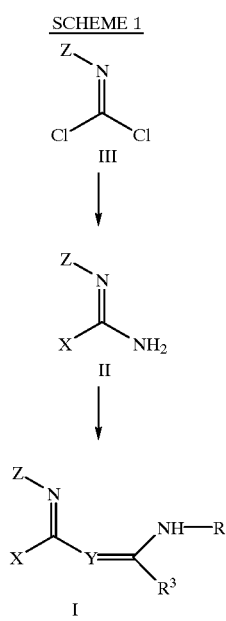
SCHEME 2
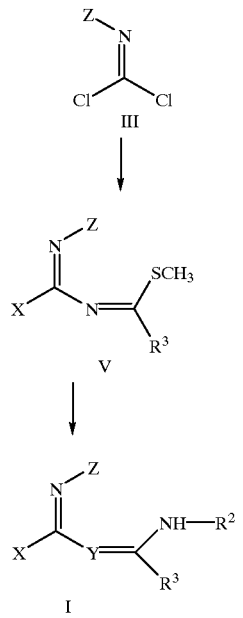
SCHEME 3
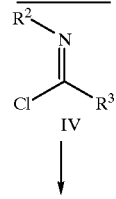
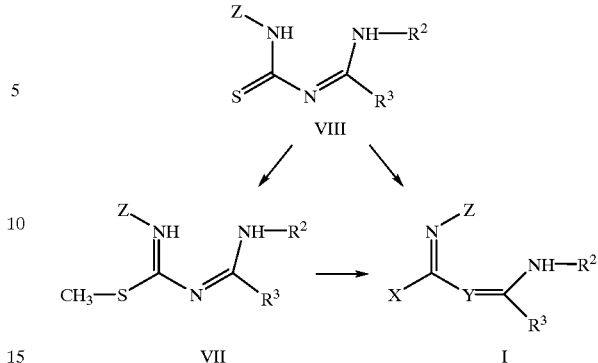
SCHEME 4
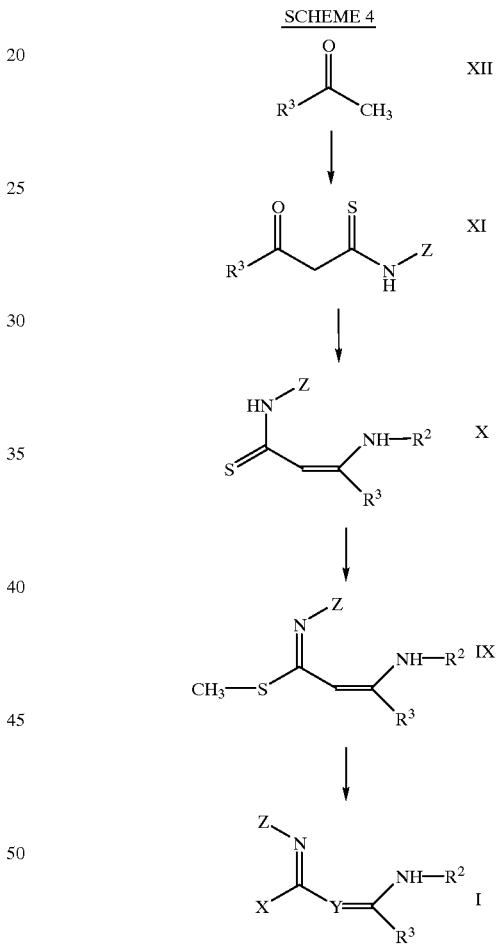
SCHEME 5
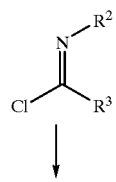

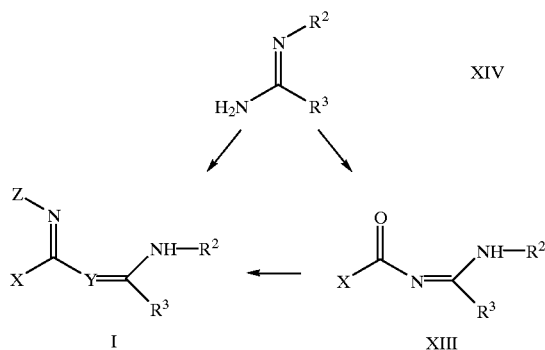

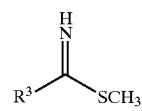

Scheme 1 refers to the preparation of compounds of the formula I, wherein Y is nitrogen, and X is $NR^4R^5$ from compounds of the formula III. Compounds of the formula III are commercially available or can be made be methods available to one of ordinary skill in the art.

A compound of the formula III is converted into a compound of the formula II by sequentially reacting the compound of the formula III with a compound of the formula X-H and a base in a reaction inert solvent followed by reaction with ammonia. Suitable reaction inert solvents include ethers such as diethyl ether, tetrahydrofuran and diisopropyl ether, acetone or acetonitrile, preferably diethyl ether. Suitable bases include triethylamine, pyridine, diisopropylethylamine, preferably triethylamine. Ammonia can be added in the form of a gas or as a solution in an organic solvent. Suitable organic solvents include alcohols such as ethanol and isopropanol, or benzene or toluene. When ammonia is added as a solution the preferred solvent is isopropanol. The temperature of the reaction during the addition of the reactant X-H may be in the range from about −78° C. to about 25° C., preferably 0° C. to about 25° C. The temperature for the reaction with ammonia is in the range from about 0° C. to about 40° C., preferably about 25° C.

The compound of formula II is converted into a compound of formula I by reaction of the compound of formula II with a strong base in a reaction inert solvent, followed by addition of a compound of the formula

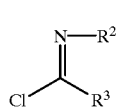

Compounds of the formula IV can be prepared according to the method described in *J. Heterocyclic Chem.*, 18, 659 (1981). Suitable bases include sodium hydride, potassium hydride and n-butyl lithium, preferably sodium hydride. Suitable solvents include ethers such as tetrahydrofuran, and diethyl ether, dimethylformamide, preferably tetrahydrofuran. The temperature during the addition of the strong base may be in the range from about 0° C. to about 35° C., preferably about 25° C. The temperature during the addition of the compound of formula IV may be in the range from about −25° C. to about 25° C., preferably 0° C. to about 25° C.

Scheme 2 refers to an alternate preparation of compounds of the formula I, wherein Y is nitrogen and X is $NR^4R^5$, from compounds of the formula III.

A compound of the formula III is converted into a compound of the formula V by sequentially reacting the compound of the formula III with a compound of the formula X-H and a base in a reaction inert solvent followed by reaction with a compound of the formula Suitable reaction inert solvents include ethers such as diethyl ether, tetrahydrofuran and diisopropyl ether, acetone or acetonitrile, preferably diethyl ether. Suitable bases include triethylamine, pyridine, diisopropylethylamine, preferably triethylamine. The compound of formula VI is preferably dissolved in a small amount of the reaction inert solvent and is then added dropwise to the reaction, after the reaction with the compound of the formula X-H is complete. Compounds of the formula VI can be made according to the methods described in *Eur. J. Med. Chem., Chim. Ther.*, 12, 365 (1977) and *Australian J. Chem.*, 30, 2225 (1977). The temperature of the reaction during the addition of the reactant X-H may be in the range from about −78° C. to about 25° C., preferably 0° C. to about 25° C. The temperature for the reaction with the compound of formula VI is in the range from about −100° C. to about 80° C., preferably about 0° C. to about 40° C. (i.e. the boiling point of the preferred solvent).

The compound of the formula V is converted into a compound of formula I by reaction with a compound of the formula $R^2NH_2$ in a reaction inert solvent at a temperature from about 25° C. to about 100° C., preferably at about 100° C. Suitable solvents include (1,4)-dioxane, tetrahydrofuran, dimethylformamide, acetonitrile or t-butanol, preferably (1,4)-dioxane or t-butanol.

Scheme 3 refers to the preparation of compounds of the formula I, wherein Y is nitrogen and X is $NR^4R^5$, from compounds of the formula IV. Compounds of the formula IV can be made according to the methods described in *J. Heterocyclic Chem.*, 18, 659 (1981).

Compounds of the formula IV are converted into compounds of the formula VIII by sequentially reacting the compound of formula IV in a reaction inert solvent with a thiocyanate followed by reaction with a compound of the formula $Z—NH_2$. Suitable thiocyanates include sodium thiocyanate or potassium thiocyanate, preferably sodium thiocyanate. Suitable solvents include acetone, ethers (such as tetrahydrofuran) and acetonitrile, preferably acetone. The temperature for the reaction with the thiocyanate is in the range from about −35° C. to about 10° C., preferably 0° C. The temperature of the reaction with the compound of the formula $Z—NH_2$ is in the range from about −35° C. to about 35° C., preferably about 25° C. Variations of the aforesaid reaction can be found in Goerdeler, et al., *Chem. Ber.*, 101, 3475 (1968).

The compound of formula VIII can be converted into a compound of formula VII by reaction with a methylating agent in a reaction inert solvent. Suitable methylating agents include methyl iodide, trimethyloxonium tetrafluoroborate or methyl trifluoromethanesulfonate, preferably methyl iodide or trimethyloxonium tetrafluoroborate. Suitable reaction inert solvents include methylene chloride, 1,2 dichloroethane or acetone, preferably acetone or methylene chloride. The temperature for the aforesaid process may be in the range from about 0° C. to about 90° C., preferably 25° C. to about 60° C.

The compound of formula VII can be converted to a compound of formula I by reaction with a compound of the formula X-H in a reaction inert solvent. Suitable reaction inert solvents include (1,4)-dioxane, acetonitrile, t-butanol or dimethylformamide, preferably (1,4)-dioxane. The temperature of the aforesaid reaction is in the range from about 25° C. to about 180° C., preferably 100° C. (i.e. the boiling point of the preferred solvent).

Alternatively, a compound of the formula VII can be converted to a compound of the formula I by reaction with a compound of the formula X-H in the presence of silver nitrate and a base in a reaction inert solvent, in the dark. Suitable bases include triethylamine, pyridine, diisopropylethylamine, preferably triethylamine. Suitable reaction inert solvents include acetonitrile, methylene chloride or 1,2-dichloroethane, preferably acetonitrile. The temperature of the aforesaid reaction is in the range from about −1 5° C. to about 60° C., preferably about 0° C. to about 25° C. Variations of the aforesaid reaction can be found in Bosin et al., *J. Org. Chem.*, 38, 1591 (1973).

Alternatively, a compound of formula I can be prepared directly from a compound of the formula VII by reaction with a compound of the formula X-H and 1-(3-dimethylaminopropyl)-3-ethylcarbodiimide hydrochloride (EDCl) in a reaction inert solvent. Suitable reaction inert solvents include dimethylformamide, tetrahydrofuran, diethyl ether or methylene chloride, preferably dimethylformamide or tetrahydrofuran. The temperature of the aforesaid reaction is in the range from about 0° C. to about 35° C., preferably about 25° C. Variations of the aforesaid reaction can be found in Atwal et al., *Tetrahedron Letters*, 30, 7313, (1989).

Scheme 4 refers to the preparation of compounds of the formula I, wherein Y is —CH— and X is $NR^4R^5$, from compounds of the formula XII. Compounds of the formula XII are commercially available or can be made by methods well known to those of ordinary skill in the art.

Referring to Scheme 4, a compound of the formula XII is converted into a compound of the formula XI by reaction with an isothiocyanate of the formula Z—N=C=S in the presence of a strong base in a reaction inert solvent. Suitable bases include lithium-, sodium- or potassium-bis (trimethylsilyl)amide, lithium dilsopropylamide, n-butyl lithium, or sodium hydride, preferably lithium bis (trimethylsilyl)amide. Suitable reaction inert solvents include tetrahydrofuran, diethylether, methylene chloride or toluene, preferably tetrahydrofuran. The temperature of the aforesaid reaction is in the range from about −78° C. to about 80° C., preferably −78° C. to about 25° C.

The compound of formula XI is converted into a compound of the formula X by reaction with a compound of the formula $R^2$—$NH_2$ and a catalytic amount (5–20%) of acid in a reaction inert solvent. Suitable acid catalysts are the hydrochloride salt of the reactant $R^2$—$NH_2$ (e.g. $R^2$—$NH_2$.HCl), toluenesulfonic acid or camphorsulphonic acid, preferably $R^2$—$NH_2$.HCl. Suitable reaction inert solvents include benzene, toluene or xylene, preferably benzene. The temperature of the aforesaid reaction is in the range of about 50° C. to about 150° C., preferably about 80° C., i.e. the boiling point of the preferred solvent. The reaction is facilitated by removal of water. Suitable dehydrating agents include azeotropic removal of water (via a Dean-Stark trap) or molecular sieves, preferably azeotropic removal of water.

The compound of formula X can be converted into a compound of formula IX by reaction with a methylating agent in a reaction inert solvent. Suitable methylating agents include methyl iodide, trimethyloxonium tetrafluoroborate or methyl trifluoromethanesulfonate, preferably trimethyloxonium tetrafluoroborate. Suitable reaction inert solvents include methylene chloride, 1,2-dichloroethane or acetone, preferably methylene chloride. The temperature for the aforesaid process may be in the range from about −10° C. to about 30° C., preferably about 0° C. to about 25° C.

The compound of formula IX is converted into a compound of formula I by reaction with a compound of the formula X-H in a reaction inert solvent. Suitable reaction inert solvents include 1,4-dioxane, acetonitrile, t-butanol or dimethylformamide, preferably (1,4)-dioxane. The temperature of the aforesaid reaction is in the range from about 25° C. to about 180° C., preferably 100° C. (i.e. the boiling point of the preferred solvent).

Alternatively, a compound of the formula IX can be converted to a compound of formula I by reaction with a compound of the formula X-H in the presence of silver nitrate and a base in a reaction inert solvent, in the dark. Suitable bases include triethylamine, pyridine, or diisopropylethylamine, preferably triethylamine. Suitable reaction inert solvents include acetonitrile, methylene chloride or 1,2-dichloroethane, preferably acetonitrile. The temperature of the aforesaid reaction is in the range from about −15° C. to about 60° C., preferably about 0° C. to about 25° C.

Scheme 5 refers to the preparation of compounds of the formula I from compounds of the formula IV. Compounds of the formula IV can be prepared according to the methods described in *J. Heterocyclic Chem.*, 18, 659 (1981).

Referring to Scheme 5, a compound of the formula IV is converted into a compound of formula XIV by reaction with ammonia in a reaction inert solvent. Suitable reaction inert solvents include alcohols such as ethanol, isopropanol, or butanol, benzene or toluene, preferably toluene. Ammonia can be added in the form of a gas or as a solution in an organic solvent. When ammonia is added as a solution the preferred solvent is the solvent that has been used as the reaction inert solvent (e.g., toluene). The temperature for the reaction is in the range from about 10° C. to about 40° C., preferably about 25° C.

The compound of formula XIV is converted into a compound of the formula XIII by reaction with a compound of the formula X—C(=O)—Cl, in the presence of a base and a catalytic amount (5–20%) of 4-dimethylaminopyridine, in a reaction inert solvent. Suitable bases include triethylamine or diisopropylethylamine, preferably triethylamine. Suitable reaction inert solvents include methylene chloride, 1,2-dichloroethane or tetrahydrofuran, preferably methylene chloride. The temperature of the aforesaid reaction is in the range from about 0° C. to about 50° C., preferably about 25° C. Compounds of the formula X—C(=O)—Cl are commercially available or can be made by the methods of Rost et al. *J. Am. Pharm. Assoc.*, 46, 290 (1957) as well as other methods well known to those of ordinary skill in the art.

Compounds of the formula XIII can be converted into compounds of the formula I by sequentially reacting the compound of formula XIII with a chlorinating agent followed by reaction with a compound of the formula Z—$NH_2$ in a reaction inert solvent. Suitable chlorinating agents include phosphorous oxychloride or phosphorous pentachloride, preferably phosphorous pentachloride. Suitable reaction inert solvents include tetrahydrofuran, methylene chloride or 1,2-dichloroethane, preferably tetrahydrofuran. The temperature of the chlorination step of the aforesaid reaction is from about 100° C. to about 150° C., preferably about 125° C. The temperature of the reaction with a compound of the formula Z—$NH_2$ is from about 0° C. to about 50° C., preferably about 25° C.

Alternatively, a compound of the formula I can be prepared directly from a compound of the formula XIV by reaction with a compound of the formula

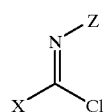

XV in a reaction inert solvent. Compounds of the formula XV can be prepared according to the method described in *J. Heterocyclic Chem.*, 18, 659 (1981). Suitable reaction inert solvents include diethyl ether, tetrahydrofuran, methylene chloride, 1,2-dichloroethane, preferably tetrahydrofuran. The temperature of the aforesaid reaction is in the range from about −20° C. to about 80° C., preferably about 25° C.

Compounds of the formula I which contain a hydroxy moiety on the X or Z (i.e. Z is not phenyl) or both rings can be prepared from compounds of the formula I in which the X and/or Z moiety contains a ketal. The ketal moiety can be introduced on any of the starting materials described in Schemes 1–5 which can support a ketone group on any or both of the X or Z rings. One of ordinary skill in the art would be able to convert the ketal to an alcohol by standard methods.

Compounds of formula I containing a hydroxy group on either or both $R^2$ or $R^3$ rings can be prepared from compounds of formula I containing a methoxy group on either or both $R^2$ or $R^3$ rings according to methods well known to those of ordinary skill in the art.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e, 1,1'-methylene-bis-(2-hydroxy-3-naphthoate)] salts.

Those compounds of the formula I which are acidic in nature are capable of forming base salts with various pharmacologically acceptable cations. Examples of such salts include the alkali metal and alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium, and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of this invention will be useful for the treatment of Alzheimer's Disease (AD) or senile dementia of the Alzheimer's type (SDAT). In AD, it has been found that the density of the $M_2$ receptors is decreased while the density of the post-synaptic $M_1$ receptors remains unaltered. A selective $m_1$ ($M_1$) muscarinic agonist would thus be efficacious at early and advanced stages of AD, and would display minimum side effects. These agents may also be useful in other conditions with disrupted cholinergic neurotransmission such as tardive dyskinesia, Pick's disease, Huntington's chorea, Freiderich's ataxia, Gilles de la Tourette disease, Down's syndrome, attention-deficit disorder (ADD), multi-infarct dementia, and age-related cognitive decline (ARCD).

The compounds of this invention may also be used in combination with a peripheral anti-muscarinic agent such as N-methyl-scopolamine to minimize peripheral side effects: in combination with anti-depressants such as imipramine in order to treat both the cognitive decline and depression associated with AD; in combination with serotonin uptake inhibitors such as Zoloft® (trademark) to treat both the cognitive decline and depression associated with AD in combination with antipsychotics such as haloperidol to treat both the cognitive decline and psychosis associated with AD; in combination with anxiolytics such as diazepam to treat both the cognitive decline and anxiety associated with AD; in combination with nicotinic agonists such as nicotine in order to stimulate both central muscarinic and nicotinic receptors; in combination with neurotrophic factors such as NGF in order to maximize cholinergic enhancement; in combination with agents which slow or arrest AD such as amyloid or tau inhibitors. These agents may also be useful in the treatment of addictions such as smoking (for cessation) and for the treatment of glaucoma.

The compounds of this invention may not only offer palliative therapy for AD, but may also slow the progression of the disease. In vitro studies have demonstrated that stimulation of the m, and $m_3$ muscarinic receptors with carbachol, a known muscarinic agonist, results in the rapid release of soluble amyloid precursor protein (APP) derivatives (Nitsch et al., *Release of Alzheimer Amyloid Precursor Derivatives Stimulated by Activation of Muscarinic Acetylcholine Receptors*, Science, 258, 304–307 (1992)). Formation of the highly insoluble Aβ peptide from APP leads to amyloidosis, resulting in neurotoxicity and the formation of neuritic plaques.

Activity of the compounds of formula I for muscarinic receptors can be determined according to the following protocol. Chinese hamster ovary cells (CHO—Ki) stably transformed to express human m1–m5 receptors can be obtained from Dr. Tom Bonner (Laboratory of Cell Biology, National Institute of Mental Health, Building 36, Rm 3A-17, National Institute of Health, Bethesda, Md. 20892). Cells are maintained in Dulbecco's Modified Eagle Medium containing 10% fetal calf serum and harvested at confluence by brief incubation in $Ca^{++}/Mg^{++}$-free phosphate-buffered saline containing 4 mM EDTA.

For ligand binding studies, cells are homogenized by sonication in distilled water and membranes are collected by centrifugation (10 minutes at 15,000×g). Membranes are incubated 45 minutes at 20–22° C. with $^3$H-N-methylscopolamine (NMS; 0.5–1.0 nM) in 0.25 ml 20 mM HEPES (N-2-hydroxyethylpiperazine-N'-2-ethane sulfonic acid), 2 mM $MgCl_2$, pH 7.4. Bound ligand is collected by rapid filtration and quantified by liquid scintillation spectroscopy. Non-specific binding is defined in the presence of 10 μM unlabeled NMS. Apparent ki for competing ligands is calculated as described by Cheng and Prusoff, *Biochem. Pharm.*, 22, 3099–3108 (1973).

Functional responses at m2 and m4 receptors can be determined by measuring inhibition of forskolin-stimulated cAMP accumulation. Harvested cells are preincubated (15 minutes at 20–22° C.) with 3-isobutyl-1-methyl-xanthine (IBMX; 0.2 mM) and then incubated (10 minutes at 20–22° C.) in a HEPES-buffered Krebs solution with test compounds in the presence of 5 μM forskolin. The reaction is stopped by the addition of 10 N acetic acid and the cAMP content of dried supernatants is determined using a scintillation proximity assay (Amersham). Carbachol is used as the standard agonist, typically providing 60–80% inhibition of the forskolin-stimulated cAMP levels.

Functional responses at $m_1$, $m_3$ and $m_5$ receptors can be determined by measuring increases in phosphotidylinositol hydrolysis. Harvested cells are preincubated (60 minutes at 37° C.) in HEPES-buffered Krebs with $^3$H-myoinositol (ARC Inc.; 7.3 μCi/ml). Labelled cells are added to test compounds and incubated 1 hour at 37° C. in the presence of 10 mM LiCl. Cells are extracted with chloroform:methanol (1:2) and the aqueous phase is loaded onto columns of DOWEX AG1-X8 ion exchange resin. Inositol phosphates (mainly IP3) are eluted with 0.1 M formic acid/1 M ammonium formate and counted.

All of the compounds of this invention, which were tested in the above functional assays, have $EC_{50}$ in the $m_2$ and $m_4$ receptor assay of about 1 nM to about 10 μM or less. All of the compounds of this invention, which were tested, have $EC_{50}$ in the m1, m3 and m5 receptor assay of about 1 picoM to about 10 μM or less.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbid acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., AD) is 0.1 to 200 mg of the active ingredient per unit dose which could be administered, for example, 1 to 4 times per day.

Aerosol formulations for treatment of the conditions referred to above (e.g., AD) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, I.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage. The compounds of this invention may exist in different polymorphic forms, i.e., different crystalline forms.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg. to about 2000 mg., preferably from about 0.1 mg. to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg. to about 2000 mg., preferably from about 1 mg. to about 200 mg. of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 μg to about 10,000 μg of the active compound of this invention, preferably from about 1 μg. to about 10 mg. of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg. to about 2000 mg. of a 5-HT re-uptake inhibitor, preferably sertraline, preferably from about 1 mg. to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg. to about 100 mg. per kg. of body weight per day of a 5-HT re-uptake inhibitor, preferably sertraline, preferably from about 0.1 mg. to about 10 mg. per kg. of body weight per day of sertraline; with from about 0.001 mg. to about 100 mg. per kg. of body weight per day of a compound of formula I, preferably from about 0.01 mg. to about 10 mg. per kg. of body weight per day of a compound of formula I, although variations will necessarily occur depending upon the conditions of the subject being treated and the particular route of administration chosen.

The following Examples illustrate the preparation of the compounds of the present invention. Commercial reagents were utilized without further purification. Melting points are uncorrected. NMR data are reported in parts per million (d) and are referenced to the deuterium lock signal from the sample solvent. Specific rotations were measured at room temperature using the sodium D line (589 nm). Room temperature refers to 20–25° C. Mass spectrum (MS) and high resolution mass spectrum (HRMS) were performed using electron impact (EI, 70 eV), chemical ionization (CI) or fast atom bombardment (FAB) conditions. Chromatography refers to column chromatography performed using 32–63 μm silica gel and executed under nitrogen pressure (flash chromatography) conditions. Purification of final compounds was carried out using buffered silica gel prepared as follows. A mixture of 125 grams of silica gel and 500 mL of 4% $KH_2PO_4$ was stirred for 1 hour and filtered. The buffered silica gel collected was air-dried and then dried in the oven at 120° C. for 48 hours or more.

EXAMPLE 1

Scheme 1

N-Phenyl-N'-(phenylimino-pyrrolidin-1-yl-methyl)-benzamidine

Step A

Intermediate of Formula II (Z=Phenyl, X=Pyrrolidine)

A solution of pyrrolidine (8.18 g, 0.115 mol) and triethylamine (11.6 g, 0.115 mol) in diethyl ether (20 mL) was added dropwise to a cold (0° C.) solution of phenyl isocyanide dichloride (20.0 g, 0.115 mol) in diethyl ether (200 mL). After addition was complete, the mixture was stirred at 0° C. for 1 hour and then allowed to warm to room temperature (20 minutes). The reaction was filtered and the filtrate was added dropwise to a saturated solution of ammonia/isopropanol (600 mL). After 1.25 hours, excess ammonium chloride was removed by filtration and the filtrate was concentrated. The residue was redissolved in isopropanol (250 mL) and hydrogen chloride (g) was bubbled through for 5 minutes. After concentration, the pale yellow gum was triturated from diethyl ether to yield an off-white solid (24.20 g, 93%), hydrochloride salt.

$^1$H-NMR (DMSO-$d_6$) δ 9.68 (s, 1H), 7.59 (s, 2H), 7.43 (m, 2H), 7.30 (m, 3H), 3.52 (br m, 4H), 1.93 (br t, 4H, J=6.6 Hz).

Step B

N-Phenyl-N'-(phenylimino-pyrrolidin-1-yl-methyl)-benzamidine

Sodium hydride (60% mineral oil dispersion, 1.1 g, 27.68 mmol) was added to a suspension of the product from Step A (free base, 6.25 g, 27.68 mmol) in tetra-hydrofuran, THF, (70 mL) at room temperature. After stirring for 15 minutes, the mixture was cooled to 0° C. and a solution of benzene carboxyimidoyl chloride, N-phenyl, (prepared according to the method described in J. Heterocyclic Chem., 18, 651 (1981)) (3.0 g, 13.84 mmol) in THF (50 mL) was added dropwise. The resulting mixture was allowed to warm to room temperature and was stirred for 16 hours (overnight). The reaction mixture was then heated to reflux for 2 hours. After cooling to room temperature, the mixture was filtered and the filtrate concentrated. The residue was dissolved in chloroform and the resulting organic layer was washed with 1N hydrochloric acid, followed by brine. The organic layer was then dried over potassium carbonate, filtered, and concentrated. The yellow soft solid obtained was dissolved in a minimum amount of acetone and diethyl ether was added. The pale yellow solid obtained was collected by filtration and dried under high vacuum to give 1.8 grams of crude material. Further purification was achieved by recrystallization (isopropanol/diethyl ether) to give the title compound (400 mg, 7%), hydrochloride salt, as an off-white solid.

Mp 246–247° C.; $^1$H-NMR (DMSO-$d_6$) δ 10.78 (s, 1H), 10.20 (s, 1H), 7.75 (br s, 2H), 7.56 (t, 1H, J=7.4 Hz), 7.40–7.47 (m, 4H), 7.11–7.27 (m, 4H), 7.06 (d, 2H, J=7.5 Hz), 6.84 (d, 2H, J=7.3 Hz), 3.63 (br s, 4H), 1.97 (br, s, 4H); CIMS $C_{24}H_{24}N_4$: 369 [(M+1)$^+$, 100].

EXAMPLE 2

Scheme 2

N-(4-Fluoro-phenyl)-N'-(phenylimino-pyrrolidin-1-yl-methyl)-benzamidine

Step A

Intermediate of Formula V ($X$=pyrrolidine; $Z$=$R_3$=Phenyl)

A solution of pyrrolidine (0.55 mL, 6.61 mmol) and triethylamine (0.92 mL, 6.61 mmol) in diethyl ether (10 mL) was added dropwise to a cold (0° C.) solution of phenyl isocyanide dichloride (0.9 mL, 6.61 mmol) in diethyl ether (15 mL). After 40 minutes, the reaction was filtered. The filtrate was re-cooled to 0° C. and a solution of benzene carboximidothioic acid, methyl ester (prepared according to the methods described in *Eur. J. Med. Chem., Chim. Ther.*, 12, 365 (1977), and *Australian J. Chem.*, 30, 2225 (1977)) (1.0 g, 6.61 mmol) in diethyl ether (5 mL) was added. The ice bath was removed and the mixture was heated to reflux for 19 hours. Solids were removed by filtration and the filtrate was concentrated. The residue obtained was washed with diethyl ether to yield (1.77 g, 76%) an off-white solid, hydrochloride salt.

$^1$H-NMR (DMSO-$d_6$) δ 10.83 (s, 1H), 7.60 (t, 1H, J=7.5 Hz), 7.46 (t, 2H, J=7.7 Hz), 7.18–7.32 (m, 3H), 7.04 (d, 2H, J=7.5 Hz), 6.87 (d, 2H, J=6.9 Hz), 3.73–3.78 (m, 2H), 3.40–3.57 (m, 2H), 2.58 (s, 3H), 1.95–2.11 (m, 4H).

Step B

N-(4-Fluoro-phenyl)-N'-(phenylimino-pyrrolidin-1-yl-methyl)-benzamidine

A mixture of the product from Step A (0.5 g, 1.39 mmol) and p-fluoroaniline (0.330 mL) in dioxane (10 mL) was heated to reflux for 23 hours. The mixture was allowed to cool to room temperature and the reaction was filtered. The title compound (0.453 g, 77%), hydrochloride salt, was obtained as a white solid.

Mp 259–260° C. (dec); $^1$H-NMR (DMSO-$d_6$) δ 10.68 (s, 1H), 9.95 (s, 1H), 7.77 (br s, 2H), 7.57 (t, 1H, J=7.4 Hz), 7.42 (t, 2H, J=7.6 Hz), 7.29 (t, 2H, J=8.7 Hz), 7.12–7.23 (m, 3H), 7.04 (d, 2H, J=7.6 Hz), 6.77 (d, 2H, J=7.2 Hz), 3.57–3.64 (m, 4H), 1.97–1.99 (m, 4H); FABMS $C_{24}H_{23}FN_4$: 387 [(M+1)$^+$, 100].

EXAMPLE 3

(Scheme 3)

N-[(2-Methyl-piperidin-1-yl)-phenylimino-methyl]-N'-phenyl-benzamidine

Step A

Intermediate of Formula VIII ($Z$=$R_2$=$R_3$=phenyl)

A solution of sodium thiocyanate (18.8 g, 0.32 mol) in acetone (400 mL) was added dropwise to a stirring solution of benzene carboxyimidoyl chloride, N-phenyl (50.0 g, 0.32 mol) in acetone (120 mL) at 0° C. After 1 hour, the reaction mixture was filtered (10–20 μ) and the filtrate was re-cooled to 0° C. Aniline (23.7 mL, 0.232 mol) was added dropwise and the reaction was allowed to warm to room temperature. After 1.5 hours, the precipitate formed was collected by filtration to yield a pale yellow solid (49.12 g, 64%).

$^1$H-NMR (DMSO-$d_6$) δ 10.61–10.88 (m, 1H), 9.80–10.21 (m, 1H), 7.40–7.75 (m, 9H), 7.21–7.38 (m, 4H), 6.97–7.15 (m, 2H)

Step B

Intermediate of Formula VII ($Z$=$R_2$=$R_3$=phenyl)

Methyl iodide (6.8 mL, 0.11 mol) was added to a suspension of the product from Step A (33.0 g, 0.1 mol) in methylene chloride (450 mL) at room temperature and then the reaction was heated to reflux for 22 hours. The reaction mixture was then cooled, filtered and the precipitate collected and dried to yield a pale yellow solid (27.7 g, 59%) as the hydroiodide salt.

$^1$H-NMR (DMSO-$d_6$) δ 11.70 (br s, 2H), 7.63–7.71 (m, 6H), 7.51 (t, 3H, J=7.8 Hz), 7.32–7.43 (m, 4H), 7.05–7.15 (m, 2H), 2.5 (s, 3H).

Step C

N-[(2-Methyl-piperidin-1-yl)-phenylimino-methyl]1-N'-phenyl-benzamidine

To a suspension of the product from Step B (1.00 g, 2.11 mmol) in 1,4-dioxane (20 mL) was added 2-methylpiperidine (0.745 mL, 6.33 mmol). The resulting solution was heated to reflux for 20 hours. The reaction was then concentrated and the residue purified by silica gel flash chromatography (gradient of 100% methylene chloride to 5% methanol-methylene chloride) to give the title compound (0.193 g, 17%), hydroiodide salt, as a pale yellow solid.

Mp 219–221° C. (dec); $^1$H-NMR (DMSO-$d_6$) 10.57 (br s, 1H), 9.64 (br s, 1H), 7.69–7.72 (m, 2H), 7.61 (t, 1H, J=7.7 Hz), 7.43–7.51 (m, 4H), 7.11–7.29 (m, 4H), 6.98 (d, 2H), 6.74 (d, 2H), 4.51–4.60 (m, 1H), 3.95–4.09 (m, 1H), 3.25–3.34 (m, 1H), 1.40–1.73 (m, 5H), 1.28 (br d, 3H, J=5.3 Hz); CIMS $C_{26}H_{28}N_4$: 397 [(M+1)$^+$, 100].

EXAMPLE 4

(Scheme 3)

N-(r1,21Oxazinan-2-yl-phenylimino-methyl)-N'-phenyl-benzamidine

Step C'

Triethylamine (0.20 mL, 1.45 mmol) followed by tetrahydrooxazine (prepared according to the methods described in King, H., *J. Chem. Soc.* 1942, 432) (0.358 g, 2.90 mmol) was added to a solution of the product from Example 3, Step B, free base. (0.5 g, 1.45 mmol) in acetonitrile (50 mL) at 0° C. A solution of silver nitrate (0.246 g, 1.45 mmol) in acetonitrile (2 mL) was added and, after 10 minutes, the ice bath was removed and the reaction allowed to stir at room temperature in the dark. After 1.5 hours, the mixture was centrifuged (3500 rpm, 10 minutes) and the supernatant was decanted, filtered (45 μ), and concentrated. Purification by flash chromatography (gradient of 100% methylene chloride to 15% methanol-methylene chloride) gave the title product (0.524 g, 86%), nitrate salt, as an off-white solid.

Mp 187–190° C.; $^1$H-NMR (DMSO-d6) δ 10.90 (br s, 1H), 10.45 (br s, 1H), 7.70–7.74 (m, 2H), 7.62 (t, 1H, J=7.5 Hz), 7.43–7.52 (m, 4H), 7.23–7.31 (m, 4H), 7.10 (d, 2H, J=7.8 Hz), 6.95 (d, 2H, J=7.4 Hz), 3.824.20 (m, 4H), 1.48–1.80 (m, 4H); CIMS $C_{24}H_{24}N_4O$: 385 [(M+1)$^+$, 100].

EXAMPLE 5

(Scheme 3)

N-(4-Methoxy-phenyl )-2,6-dimethyl-N'-[(2-methyl-piperidin-1-yl)-phenylimino-methyl]-benzamidine Step A'

Intermediate of Formula IV ($R_2$=(4)-methoxyphenyl: $R_3$=2,6-Dimethylphenyl)

A neat mixture of 2,6-dimethylbenzamide, N-4methoxyphenyl (6.60 g, 25.85 mmol) and phosphorous pentachloride (5.38 g, 25.85) was heated to 120° C. The solution obtained was stirred for 20 minutes. Toluene was added and the mixture was concentrated (twice). The oil obtained was immediately used as such in the next step.

Step A

Intermediate of Formula VIII ($R_2$=(4)-methoxyphenyl; $R_3$=2,6-Dimethyl phenyl; $Z$=phenyl)

The same procedure described in Example 3, Step A above was followed with sodium thiocyanate (2.10 g, 25.85 mmol), the product from Step A' (crude, 25.85 mmol), and aniline (3.53 mL, 38.78 mmol) to yield a white solid (1.75 g, 18%).

¹H-NMR (CDCl₃) δ 7.80–7.84 (m, 3H,), 7.42 (t, 2H, J=7.9 Hz), 7.18–7.28 (m, 2H), 7.02 (d, 2H, J=7.7 Hz), 6.67 (s, 4H), 3.71 (s, 3H), 2.29 (s, 6H).

N-(4-Methoxy-phenyl)-2,6-dimethyl-N'-[(2-methyl-piperidin-1 -yl)-phenylimino-methyl]-benzamidine Step C"

To a solution of the product from Step A, above, (0.50 g, 1.28 mmol) in dimethylformamide (6 mL) was added 2-methylpiperidine (0.33 g, 2.82 mmol) and 1-(3-dimethylaminopropyl)-3-ethylcarbodiimide, hydrochloride (EDCI) (0.27 g, 1.41 mmol). The resulting mixture was stirred at room temperature for 16 hours (overnight). The reaction was concentrated in vacuo and the residue was partitioned between ethyl acetate and saturated sodium bicarbonate. The separated organic layer was dried (potassium carbonate), filtered, and ethanolic hydrogen chloride was added. After concentration, the residue was purified by silica gel flash chromatography (gradient from 100% methylene chloride to 15% methanol-methylene chloride) gave the title compound (0.475 g, 76%), hydrochloride salt, as a white solid.

Mp 190–192° C. (dec); ¹H-NMR (CDCl₃) δ 7.52 (d, 2H, J=7.6 Hz), 7.27 (t, 2H, J=7.3 Hz), 7.16 (t, 1H, J=7.4 Hz), 7.03 (t, 1H, J=7.6 Hz), 6.83 (d, 1H, J=7.1 Hz), 6.76 (d, 1 H, J=7.5 Hz), 6.68 (d, 2H, J=9.0 Hz), 6.51 (d, 2H, J=9.0 Hz), 4.90 (br s, 1H), 4.32 (br d, 1H, J=13.6 Hz), 1.62–1.95 (m, 5H), 1.53 (d, 3H, J=7.0 Hz), 1.30–1.41 (m, 2H); CIMS $C_{29}H_{34}N_4O$: 455 [(M+1)⁺, 100].

EXAMPLE 6

(Scheme 4)

(3-Phenylimino-3-[2-methyl]piperidin-1-yl-1-o-tolyl-propenyl)-(4-fluoro-phenyl)-amine Step A Intermediate of Formula XI ($R_3$=2-Methylphenyl: Z=phenyl)

A solution of lithium bis(trimethylsilyl)amide (1M in tetrahydrofuran, 22.36 mL, 22.36 mmol) was added to a solution of 2-methyl acetophenone (3.0 g, 22.36 mmol) in tetrahydrofuran (220 mL) at −78° C. After 15 minutes, phenyl isocyanide (2.67 mL, 22.36 mmol) was added and the resulting mixture was kept at −78° C. for 0.5 hour and then at room temperature overnight. To the reaction was added 1N hydrochloric acid and the mixture was extracted with methylene chloride. The separated organic layer was dried (potassium carbonate), filtered, and concentrated. The residue was purified by flash chromatography (5% ethyl acetate-hexane) to yield a bright yellow solid (4.14 g, 69%).

¹H-NMR (CDCl₃) (2:1 mixture of tautomers) δ 14.79 (s, 1H), 10.87 (br s, 0.5H), 8.21 (s, 1H), 7.92 (d, 0.5H, J=8.1 Hz), 7.80 (d, 1H, J=7.7 Hz), 7.16–7.49 (m, 12H), 5.80 (s, 1H). 4.56 (s, 1H), 2.57 (s, 1.5H), 2.44 (s, 3H).

Step B

Intermediate of Formula X ($R_2$=4-Fluorophenyl: $R_3$=2-Methylphenyl: Z=phenyl).

A mixture of the product of Step A above (3.0 g, 11.14 mmol), 4-fluoroaniline (1.16 mL, 12.25 mmol), and 4-fluoroaniline hydrochloride (0.164 g, 1.11 mmol) in benzene (100 mL) was heated to reflux with removal of water (Dean-Stark trap). After 18 hours, additional 4-fluoroaniline (0.264 mL, 2.79 mmol), and 4-fluoroaniline hydrochloride (0.164 g, 1.11 mmol) were added. Reflux was continued for another 30 hours (48 hours total reaction time). The mixture was concentrated and the residue was triturated from diethyl ether to give a yellow solid. This solid was redissolved in methylene chloride and the organic layer was washed with brine, dried (potassium carbonate), filtered, and concentrated to yield a yellow solid (1.93 g, 48%).

¹H-NMR (CDCl₃) δ 13.65 (s, 1H), 7.97 (s, 1H), 7.15–7.40 (m, 8H), 7.07 (d, 1H, J=7.3 Hz), 6.65–6.82 (m, 4H), 5.43 (s, 1H), 2.11 (s, 3H).

Step C

Intermediate of Formula IX ($R_2$=4-Fluorophenyl; $R_3$=2-Methylphenyl; Z=phenyl).

Trimethyloxonium tetrafluoroborate (0.673 g, 4.55 mmol) was added to a solution of the product from Step B, above, (1.50 g, 4.14 mmol) in methylene chloride (50 mL) at 0° C. After 15 minutes, the ice bath was removed and the reaction was allowed to stir at room temperature for 1.25 hours. The reaction mixture was washed with saturated potassium carbonate and the separated organic layer was dried (potassium carbonate), filtered, and concentrated. The residue was purified by flash chromatography (methylene chloride) to yield a white foam (1.28 g, 82%).

Mp 179–181° C.; ¹H-NMR (CDCl₃) δ 12.47 (s, 1 H), 7.22–7.41 (m, 5H), 7.12–7.14 (m, 2H), 7.04 (d, 2H, J=7.7 Hz), 6.71 (t, 2H, J=8.7 Hz), 6.54–6.56 (m, 2H), 5.02 (s, 1H), 2.35 (s, 3H), 2.18 (s, 3H); CIMS 428 [(M+1)+, 100].

Step D (3-Phenylimino-3-[2-methyl]piperidin1-yl-1-o-tolyl-propenyl)-(4-fluoro-phenyl)-amine The same procedure described in Example 4C' was followed with the product from Step C, above, (0.40 g, 1.06 mmol), 2-methylpiperidine (0.187 mL, 1.59 mmol), triethylamine (0.147 mL, 1.06 mmol), and silver nitrate (0.180 g, 1.06 mmol) in acetonitrile (20 mL) to give the title compound (0.395 g, 76%), nitrate salt, as a pale yellow solid.

¹H-NMR (CDCl₃) δ 10.35 (br s, 1H), 8.95 (br s, 1H), 7.33 (d, 2H, J=7.5 Hz), 6.99–7.22 (m, 6H), 6.93 (d, 1H, J=7.2 Hz), 6.54 (t, 2H, J=8.7 Hz), 6.13 (dd, 2H, J=9.0 Hz, J =4.7 Hz), 4.574.72 (m, 1H), 4.52 (s, 1H), 4.104.22 (m, 1H), 3.41–3.58 (m, 1H), 1.96 (s, 3H), 1.62–1.95 (m, 6H) 1.44 (br d, 3H, J=6.3 Hz), CIMS $C_{28}H_{30}FN_3$: 428 [(M+1)⁺, 100.

EXAMPLE 7

(Scheme 5)

N-[Cyclohexylimino-(2-methyl-piperidin-1-yl)-methyl]-N'-(4-fluoro-phenyl)-2,6-dimethyl-benzamidine Step A Intermediate of Formula XIV ($R_2$=4-Fluorophenyl: R=2,6-dimethylphenyl)

A neat mixture of 2,6-dimethylbenzamide, N-4-fluorophenyl (6.60 g, 25.85 mmol) and phosphorous pentachloride (5.38 g, 25.85) was heated to 120° C. The solution obtained was stirred for 20 minutes. Toluene was added and the mixture was concentrated (twice). The oil obtained was dissolved in toluene (270 mL) and cooled to 0° C. Ammonia (g) was bubbled through the reaction mixture for 0.5 hours. The reaction was filtered and the filtrate was concentrated. The residue obtained was purified by silica gel flash chromatography (gradient from 50% ethyl acetate-hexane to 100% ethyl acetate) to yield an off-white solid (5.02 g, 56%).

¹H-NMR (CDCl₃, mixture of rotomers) δ 6.99–7.22 (m, 5H), 6.60–6.73 (m, 2H), 4.79 (br s, 2H), 2.48 (s, 3H), 2.30 (s, 3H).

Step B

Intermediate of Formula XIII (X=2-methylpiperidine, $R_3$=4-fluorophenyl; $R_2$=2,6-dimethyl).

Triethylamine (1.2 mL, 8.25 mmol), dimethylaminopyridine (0.10 g, 0.825 mmol), and the product from Step A (2.0 g, 8.25 mmol) were added to a solution of 2-methylpiperidine carbamoyl chloride (prepared according to the method of Rost et al., *J. Am. Pharm. Assoc.*, 46, 290 (1957)) (1.33 g, 8.25 mmol) in methylene chloride. The resulting mixture was allowed to stir at room temperature for 4 days. The mixture was washed with saturated potassium carbonate, dried (potassium carbonate), filtered, and concentrated. Purification by flash chromatography (gradient from 10% ethyl acetate-hexane to 100% ethyl acetate) yielded a white foamy solid (0.832 g, 28%).

¹H-NMR (CDCl₃, mixture of rotomers) δ 7.15 (t, 1H, J=7.6 Hz), 6.97 (br t, 2H, J=9.8 Hz), 6.76 (t, 2H, J=8.6 Hz), 6.60–6.64 (m, 2H), 4.32–5.15 (m, 2H), 2.80–3.02 (m, 1H), 2.28 (s, 3H), 2.21 (s, 3H), 1.40–1.75 (m, 6H), 1.12–1.30 (m, 3H).

Step C

N-[Cyclohexylimino-(2-methyl-piperidin-1-yl)-methyl]-N'-(4-fluoro-phenyl)-2,6-dimethyl-benzamidine A neat mixture of the product from Step 8 (0.20 g, 0.544 mmol) and phosphorous pentachloride (0.113 g, 0.544 mmol) was heated to 125° C. and the melt obtained was stirred for 1 hour. Toluene was added and the mixture was concentrated (twice). The residue was dissolved in tetrahydrofuran (8 mL) and cyclohexylamine (0.27 g, 2.72 mmol) was added. The mixture obtained was stirred at room temperature for 2 hours. The reaction was filtered and the filtrate was concentrated. The residue was purified by silica gel flash chromatography (gradient of 100% methylene chloride to 5% methanol-methylene chloride) to give the title compound (0.084 g, 34%), hydrochloride salt, as a white solid.

Mp 167–168° C.; ¹H-NMR (CDCl₃, mixture of rotomers) δ 10.90 (br s, 1H), 7.17–7.27 (m, 2H), 6.93–7.06 (m, 3H), 6.76 (t, 2H, J=8.5 Hz), 4.604.75 (m, 1H), 4.03–4.14 (m, 1H), 3.70–3.85 (m, 1H), 3.38–3.51 (m, 1H), 2.42 (s, 3H), 2.27 (s, 3H), 1.96–2.17 (m, 2H), 1.40–1.80 (m, 14H), 1.17–1.37 (m, 3H); EIMS $C_{28}H_{37}FN_4$: 448 (M⁺).

EXAMPLE 8

N-(4-Fluoro-phenyl)-2-methyl-N'-[(4-oxo-piperidin-1-yl)-phenylimino-methyl]-benzamidine The procedure described in Example 5, Step C'', was followed with a compound of the formula VII (wherein $R_2$=4-fluorophenyl; $R_3$=2-methylphenyl; Z=phenyl) (0.40 g, 1.10 mmol), 1,4-dioxa-8-azaspiro[4.5]decane (0.347 9, 2.42 mmol), and EDCl (0.232 g, 1.21 mmol) in dimethylformamide (6 mL) to yield N-[(1,4-dioxa-8-aza-spiro (4.5]dec-8-yl)phenylimino-methyl]-N'-(4-fluorophenyl)-2-methyl benzamidine (0.388 g, 69%) as a white solid.

¹H-NMR (DMSO-d₆) δ 10.58 (br s, 1H), 10.15 (br s,1 H), 7.78–7.87 (m, 2H), 7.11–7.48 (m. 8H), 6.91 (d, 1H, J=6.3 Hz), 6.81 (d, 2H, J=7.0 Hz) 3.95 (s, 4H), 3.77 (br s, 4H). 1.79 (brs, 4H), 1.66 (s, 3H).

A solution of the above product (0.350 g, 0.688 mmol) in 90% trifluoroacetic acid/water (8 mL) was stirred at room temperature for 5.75 hours. The solution was concentrated and the residue was partitioned between methylene chloride and saturated potassium carbonate. The organic layer was dried (potassium carbonate), filtered, and concentrated. The residue was converted to the hydrochloride salt by dissolving in diethyl ether and bubbling hydrogen chloride (g). The precipitate obtained was collected and dried to give the title compound (0.262 g, 82%), hydrochloride salt, as an off-white solid.

Mp 234–235° C.; ¹H-NMR (DMSO-d₆) δ 10.63 (s, 1H), 10.22 (s, 1H), 7.79–7.88 (m, 2H), 7.45 (t, 1H, J=7.4 Hz), 7.13–7.39 (m, 7H), 6.93 (d, 1 H, J=7.4 Hz), 6.83 (d, 2H, J=7.9 Hz), 3.904.12 (m, 4H) 2.65 (t, 4H, J=5.8 Hz), 1.63 (s, 3H); CIMS $C_{26}H_{25}FN_4O$: 429 [(M+1)⁺, 100].

EXAMPLE 9

N-(4-Fluoro-phenyl)-N'-[(4-hydroxy-piperidin-1-yl)-phenylimino-methyl]-2,6-dimethyl-benzamidine Sodium borohydride (0.006 g, 0.152 mmol) was added to a solution of the product from Example 8, free base, (0.067 g, 0.152 mmol) in ethanol (6 mL) and the mixture was stirred at room temperature for 2 hours. Saturated ammonium chloride was added and the mixture was extracted with methylene chloride (twice). The organic layer was dried (potassium carbonate), filtered, and concentrated. The residue was dissolved in dioxane and hydrogen chloride (g) was bubbled through. After removal of volatiles, the salt obtained was purified by silica gel flash chromatography to give the title compound (0.033 g, 45%), hydrochloride salt, as an off-white solid.

Mp 163–165° C.; ¹H-NMR (CDCl₃, mixture of rotomers) δ 7.48 (d, 2H, J=7.2 Hz), 7.29–7.34 (m, 3H), 7.06 (t, 1 H, J=7.6 Hz), 6.82 (d, 2H, J=7.6 Hz), 6.62–6.79 (m, 4H) 4.10–4.36 (m, 3H), 3.73–3.98 (m, 2H), 1.91–2.22 (m, 6H), 1.60–1.81 (m, 4H); CIMS $C_{27}H_{29}FN_3O$: 445 [(M+1)⁺, 100].

EXAMPLE 10

N-(4-Hydroxy-phenyl)-2,6-dimethyl-N'-[2-methyl-piperdin-1-yl)-phenylimino-methyl]-benzamidine A solution of the product from Example 5, Step C' (0.04 g, 0.081 mmol) in 48% aqueous hydrobromic acid (3 mL) was heated to 110° C. for 4 hours. The cooled reaction mixture was made basic by addition of saturated sodium bicarbonate. The resulting mixture was extracted with methylene chloride and the separated organic layer was dried (potassium carbonate), filtered, and concentrated. Ethanolic hydrogen chloride was added to the residue and after stirring for 15 minutes, volatiles were removed under reduced pressure. The salt obtained was triturated from diethyl ether to give the title compound (0.034 g, 87%), hydrochloride salt, as a pale yellow solid.

Mp 216–218° C.; ¹H-NMR (DMSO-d₆, mixture of rotomers) 10.60 (s, 1H), 9.53 (s, 1H), 7.51 (d, 2H, J=8.5 Hz), 7.36–7.45 (m, 1H), 7.21–7.30 (m, 2H), 6.95–7.12 (m, 3H), 6.87 (d, 2H, J=8.7 Hz), 6.70 (d, 2H, J=7.5 Hz), 4.414.53 (m, 1H), 3.88–4.01 (m, 1H), 3.13–3.28 (m, 1H), 1.95 (s, 3H), 1.76 (s, 3H), 1.40–1.73 (m, 6H), 1.19–1.28 (m, 3H); CIMS $C_{28}H_{32}N_4O$: 441 [(M+1)⁺, 100].

EXAMPLE 11

(Scheme 5)

N-(4-Fluoro-phenyl)-2-methyl-N'-[(1-methyl-cyclohexyl)-phenylimino-methyl]-benzamidine Step A Intermediate of Formula XIV ($R_2$=4-fluorophenyl; $R_3$=2-methylphenyl)

A neat mixture of 2-methylbenzamide, N-4-fluorophenyl (4.0 g, 17.47 mmol) and phosphorous pentachloride (3.64 g, 17.47 mmol) was heated at 120° C. for 30 minutes. Toluene was added and the mixture was concentrated (twice). The oil obtained was dissolved in diethyl ether (50 mL) and cooled to 0° C. Ammonia (g) was bubbled through the reaction mixture for 20 minutes. The reaction was filtered and the filtrate concentrated. The residue was purified by silica gel flash chromatography (gradient from 100% chloroform to 5% methanol-chloroform) to yield a white solid (1.31 g, 33%).

¹H NMR (CDCl₃) δ 7.45–7.47 (m, 1H), 7.22–7.25 (m, 2H), 7.00–7.09 (m, 2H), 6.91–6.98 (m, 2H), 6.74–6.78 (m, 1H), 4.714.74 (br s, 2H), 2.53 (br s, 3H).

Step B

N-(4-Fluoro-phenyl)-2-methyl-N'-[(1-methyl-cyclohexyl)-phenylimino-methyl]-benzamidine A neat mixture of 1-methyl-cyclohexylcarboxamide, N-phenyl (0.22 g, 1.0 mmol) and phosphorous pentachloride (0.21 g, 1.0 mmol) was heated at 120° C. for 40 minutes. Toluene was then added and the mixture was concentrated (twice). The residue was dissolved in tetrahydrofuran (10 mL) and the product from Step A (0.46 g, 2 mmol) was added. The reaction was stirred at room temperature for 18 hours. The mixture was then filtered and the filtrate concentrated. Purification by flash chromatography (chloroform) yielded the title compound (0.22 g, 52%) as a white solid.

Mp 210–211 ° C.; ¹H NMR (CDCl₃) 7.26 (t, 2H, J=8 Hz), 6.88–7.14 (m, 7H), 6.70 (t, 2H, J=8 Hz), 6.43–6.46 (m, 2H), 2.02–2.14 (m, 1H), 1.44–1.65 (m, 12H), 1.33 (s, 3H); EIMS $C_{28}H_{30}FN_3$: 427 (M+).

TABLE 1

| | Y | X | Z | R² (phenyl) | R³ (phenyl) | Method (yield %)[i] | mp (° C.) | MS[h] |
|---|---|---|---|---|---|---|---|---|
| 12 | N | piperidine[f] | phenyl | H | H | Ex 3 (17)[a] | 198–200 (d) | 383 (FAB) |
| 13 | N | thiomorpholine[f] | phenyl | H | H | Ex 3 (17)[b] | 216–218 (d) | 401 (FAB) |
| 14 | N | diethylamine[f] | phenyl | 4-methoxy | H | Ex 3 (21)[b] | 222–224 (d) | 371 (FAB) |
| 15 | N | pyrrolidine | phenyl | 4-methoxy | H | Ex 2 (78)[a] | 244–245 | 398 (EI) |
| 16 | N | pyrrolidine | phenyl | 4-chloro | H | Ex 2 (82) | 219–221 | 403 (FAB) |
| 17 | N | hexamethyleneimine[f] | phenyl | H | H | Ex 3 (60) | 228–229 | 397 (FAB) |
| 18 | N | hexamethyleneimine[f] | phenyl | 4-methoxy | H | Ex 2 (70)[a] | 241–243 | 426 (EI) |
| 19 | N | hexamethyleneimine[f] | phenyl | 4-fluoro | H | Ex 2 (77) | >228 (d) | 414 (FAB) |
| 20 | N | pyrrolidine | phenyl | H | 2-methyl | Ex 3 (32)[b] | 191–192 | 383 (FAB) |
| 21 | N | 4-methyl-piperidine[f] | phenyl | H | H | Ex 3 (22) | 192–195 (d) | 397 (FAB) |
| 22 | N | heptmethyleneimine[f] | phenyl | H | H | Ex (27) | 252–253 (d) | 411 (FAB) |
| 23 | N | 3-methyl-piperidine[f] | phenyl | H | H | Ex 3 (34) | 179–182 (d) | 397 (FAB) |
| 24 | N | 4-hydroxy-piperidine | phenyl | H | 2-methyl | Ex 3 (45)[b] | 218–220 | 413 (FAB) |
| 25 | N | pyrrolidine | 4-fluorophenyl | H | H | Ex 3 (28)[b] | 242–243 | 387 (CI) |
| 26 | N | 4-hydroxy-piperidine | phenyl | 4-fluoro | 2-methyl | Ex 3 (43)[b] | 228–230 (d) | 431 (FAB) |
| 27 | N | pyrrolidine | 2-fluorophenyl | H | H | Ex 3 (10)[b] | 254–255 | 387 (CI) |
| 28 | N | 2-methyl-piperidine | phenyl | 4-fluoro | 2-methyl | Ex (3 (39)[b] | 173–175 | 429 (CI) |
| 29 | N | 4-hydroxy-piperidine | 2-fluorophenyl | H | 2-methyl | Ex 3 (19)[b] | 224–225 | 430 (EI) |
| 30 | N | pyrrolidine | phenyl | 2-chloro | H | Ex 3 (13)[b] | 228–230 | 403 (CI) |
| 31 | N | pyrrolidine[f] | phenyl | H | 2,6-dimethyl | Ex 3 (20)[b] | 255–257 | 397 (CI) |
| 32 | N | (−)-2-methyl-piperidine[f,j] | phenyl | H | H | Ex 3 (28) | 181–183 | 397 (CI) |
| 33 | N | (+)-2-methyl-methyl-piperidine[f,k] | phenyl | H | H | Ex 3 (43) | 180–182 | 397 (CI) |
| 34 | N | hexamethyleneimine | phenyl | 4-fluoro | 2-methy | Ex 3 (55) | 240–242 | 428 (EI) |
| 35 | N | 2-methyl-piperidine | phenyl | 4-fluoro | 2,6-dimethyl | Ex 3 (28) | 181–183 | 443 (CI) |
| 36 | N | 4-hydroxy-piperidine | 2-fluorophenyl | 4-fluoro | 2-methyl | Ex 3 (62) | 174–175 | 448 (CI) |
| 37 | N | 2-methyl-piperidine | phenyl | 4-fluoro | 2-chloro | Ex 4 (70) | 145–147 | 449 (CI) |
| 38 | N | 3-hydroxy-piperidine[g] | phenyl | H | H | Ex 4 (73) | 189–192 | 399 (CI) |
| 39 | N | pyrrolidine[g] | phenyl | H | 2-fluoro | Ex 4 (68) | 194–196 | 387 (CI) |
| 40 | N | 2-methyl-piperidine[g] | 4-pyridine | 4-fluoro | 2-methyl | Ex 4 (56) | 209–210 (d) | 430 (CI) |
| 41 | N | 4-ketal-pipendine | phenyl | H | H | Ex 4 (52) | 210–212 | 442 (CI) |
| 42 | N | 1,2-tetrahydrooxazine | phenyl | 4-fluoro | 2-methyl | Ex 4 (32) | 199–200 (d) | 417 (CI) |
| 43 | N | 2-methyl-piperidine | 4-fluorophenyl | 4-fluoro | 2,6-dimethyl | Ex 4 (56) | 162–164 (d) | 461 (CI) |
| 44 | N | 2-methyl-piperidine[g] | phenyl | 4-fluoro | 2,6-difluoro | Ex 4 (44) | 163–165 (d) | 451 (CI) |
| 45 | N | 2-methyl-piperidine | phenyl | 4-fluoro | 2,6-dichloro | Ex 4 (58) | 153–155 (d) | 483 (CI) |
| 46 | N | 2-methyl-piperidine | 4-chlorophenyl | 4-fluoro | 2,6-dimethyl | Ex 4 (79) | 149–151 (d) | 477 (CI) |
| 47 | N | 1-adamantine | phenyl | 4-fluoro | 2-methyl | Ex 11 (51) | 219–221 | 465 (EI) |
| 48 | N | 2,6-dimethyl-piperidine | phenyl | 4-fluoro | 2,6-dimethyl | Ex 4 (89) | 172–174 (d) | 467 (CI) |
| 49 | N | hexamethyleneimine | 4-fluorophenyl | 4-fluoro | 2,6-dimethyl | Ex 4 (74) | 155–157 | 461 (CI) |
| 50 | N | 1,2-tetrahydrooxazine | 4-fluorophenyl | 4-fluoro | 2,6-dimethyl | Ex 4 (29) | 213–214 | 449 (CI) |
| 51 | N | 2-methyl-piperidine[g] | 4-fluorophenyl | 4-fluoro | 2,6-difluoro | Ex 4 (56) | 171–173 | 469 (CI) |
| 52 | N | 2,6-dimethyl-piperidine[g] | 4-fluorophenyl | 4-fluoro | 2,6-difluoro | Ex 4 (56) | 172–174 | 483 (CI) |
| 53 | N | hexamethyleneimine | phenyl | 4-fluoro | 2,6-dimethyl | Ex 4 (44) | 243–245 | 443 (CI) |
| 54 | N | 2,6-dimethyl-piperidine | 4-fluorophenyl | 4-fluoro | 2,6-dimethyl | Ex 4 (82) | 180–181 | 469 (CI) |
| 55 | N | 2,6-dimethyl-piperidine[g] | phenyl | 4–fluoro | 2,6-difluoro | Ex 4 (62) | 175–177 | 483 (CI) |
| 56 | N | hexamethyleneimine[g] | phenyl | 4–fluoro | 2,6-difluoro | Ex 4 (54) | 171–173 | 451 (CI) |
| 57 | N | hexamethyleneimine | 4-fluorophenyl | 4-fluoro | 2,6-difluoro | Ex 5 (30) | 216–218 | 469 (CI) |
| 58 | N | 2-ethyl-piperidine | phenyl | 4-fluoro | 2,6-dimethyl | Ex 5 (56) | 137–139 (d) | 457 (CI) |
| 59 | N | trans-2,6-dimethyl-piperidine | phenyl | 4-fluoro | 2,6-dimethyl | Ex 5 (67) | 165–167 (d) | 457 (CI) |
| 60 | N | 2-methyl-piperidine | phenyl | 4-methyloxy | 2-methyl | Ex 5 (77) | 162–164 (d) | 441 (CI) |
| 61 | N | 1,2-tetrahydrooxazine | phenyl | 4-fluoro | 2,6-dimethyl | Ex 5 (58) | 212–214 (d) | 431 (CI) |
| 62 | N | 3-hydroxy-piperidine | phenyl | 4-fluoro | 2,6-dimethyl | Ex 5 (53) | 196–198 (d) | 444 (EI) |
| 63 | N | 4-keto-piperidine | phenyl | 4-fluoro | 2,6-dimethyl | Ex 8 (65) | 228–229 (d) | 443 (CI) |
| 64 | N | 2-methyl-piperidine | 4-NH₂-phenyl | 4-fluoro | 2,6-dimethyl | | 179–181 | |
| 65 | N | 2-methyl-4-keto-piperidine | phenyl | 4-fluoro | 2,6-dimethyl | Ex 8 (91) | 215–217 | 457 (CI) |
| 66 | N | 3-hydroxy-piperidine | phenyl | 4-fluoro | 2-methyl | Ex 4 (50) | >150 | 431 (CI) |
| 67 | N | 1,2-tetrahydrooxazine | phenyl | 4-methoxy | 2,6-dimethyl | Ex 5 (70) | 214–215 | 443 (CI) |
| 68 | N | hexamethyleneimine | phenyl | 4-methoxy | 2,6-dimethyl | Ex 5 (48) | 228–230 (d) | 455 (CI) |
| 69 | N | 2-methyl-4-keto-piperidine | phenyl | 4-fluoro | 2-methyl | Ex 8 (87) | >143 | 441 (CI) |
| 70 | N | 2-methyl-piperidine | 3-NH₂-phenyl | 4-fluoro | 2,6-dimethyl | Ex 7 (4) | 210–213 | 458 (CI) |
| 71 | N | 4-hydroxy-piperidine | phenyl | 4-fluoro | 2,6-dimethyl | Ex 9 (45) | 163–165 | 445 (CI) |
| 72 | N | 2-methyl-4-hydroxy-piperidine | phenyl | 4-fluoro | 2,6-dimethyl | Ex 9 (33) | 163–166 (d) | 459 (CI) |
| 73 | N | 2-methyl-piperidine | 3-NH₂-phenyl | 4-OCF₃ | 2,6-dimethyl | Ex 7 (11) | 170–172 | 525 (CI) |
| 74 | N | 2-methyl-piperidine | phenyl | 4-OCF₃ | 2,6-dimethyl | Ex 7 (25) | 148–150 | 510 (CI) |
| 75 | N | 2-methyl-piperidine | 2-methylphenyl | 4-fluoro | 2-methyl | Ex 7 (17) | 171–173 (d) | 444 (CI) |
| 76 | N | morpholine | phenyl | 4–fluoro | 2,6-dimethyl | Ex 5 (79) | 249–251 (d) | 431 (CI) |
| 77 | N | 2-methyl-piperidine | 3-methylphenyl | 4-fluoro | 2,6-dimethyl | Ex 7 (16) | 140–142 | 458 (CI) |
| 78 | N | 2-methyl-piperidine | 3-fluorophenyl | 4-fluoro | 2,6-dimethyl | Ex 7 (25) | 143–147 | 462 (CI) |
| 79 | N | 2-methyl-piperidine | 2-chlorophenyl | 4-fluoro | 2-methyl | Ex 5 (97) | 208–210 | 462 (CI) |
| | | | | | | | | 464 (CI) |
| 80 | N | 2-methyl-piperidine | 2-methoxyphenyl | 4-fluoro | 2-methyl | Ex 5 (80) | 150–152 | 460 (CI) |
| 81 | N | 2-methyl-piperidine | 3-methoxyphenyl | 4-fluoro | 2,6-dimethyl | Ex 3 (54) | 199–201 | 474 (CI) |
| 82 | N | trans-2-methyl-4-hydroxy-piperidine | phenyl | 4-fluoro | 2,6-dimethyl | Ex 5 (54)[c] | 169–172 | 459 (EI) |
| 83 | N | cis-2-methyl-4-hydroxy-piperidine | phenyl | 4-fluoro | 2,6-dimethyl | Ex 5 (65)[d] | 165–167 | 460 (CI) |
| 84 | N | 2-methyl-piperidine | 2-methylphenyl | 4-fluoro | 2,6-dimethyl | Ex 5 (51) | 206–208 | 457 (CI) |
| 85 | N | 2-methyl-piperidine | 2-chlorophenyl | 4-fluoro | 2,6-dimethyl | Ex 5 (52) | 207–209 | 477 (CI) |
| 86 | N | 2-methyl-piperidine | 3-pyridinyl | 4-fluoro | 2,6-dimethyl | Ex 5 (57)[c] | 207–210 | 444 (CI) |

TABLE 1-continued

| | Y | X | Z | R² (phenyl) | R³ (phenyl) | Method (yield %)[i] | mp (° C.) | MS[h] |
|---|---|---|---|---|---|---|---|---|
| 87 | CH | pyrrolidine[g] | phenyl | H | H | Ex 6 (41) | 184–186 | 368 (Cl) |
| 88 | CH | thiazolidine | phenyl | H | H | Ex 3 (10) | amorphous | 386 (EI) |
| 89 | CH | 2-methyl-piperidine[g] | phenyl | 4-fluoro | 2-methyl | Ex 6 (76) | 179–181 | 428 (Cl) |
| 90 | CH | 2-methyl-piperidine[g] | phenyl | 4-fluoro | 2-chloro | Ex 6 (76) | 152–155 | 448 (Cl) |
| 91 | CH | 1,2-tetrahydrooxazine[g] | phenyl | 4-fluoro | 2-methyl | Ex 6 (42) | 151–153 | 416 (Cl) |
| 92 | CH | 2-methyl-piperidine[g] | 4-fluorophenyl | 4-fluoro | 2-methyl | Ex 6 (80) | >90 (d) | 446 (Cl) |
| 93 | CH | 2-methyl-piperidine | phenyl | H | H | Ex 6 (60) | 157–158 | 396 (Cl) |
| 94 | CH | 1,2-tetrahydrooxazine | phenyl | 4-methoxy | 2-methyl | Ex 6 (24) | 192–194 | 428 (Cl) |
| 95 | CH | 1,2-tetrahydrooxazine | cyclohexyl | 2–fluoro | 2-methyl | Ex 6 (70) | 171–172 | 422 (Cl) |
| 96 | N | 1-methylcyclohexyl | cyclohexyl | 4-fluoro | 2-methyl | Ex 11 (10) | 127–129 | 433 (EI) |
| 97 | N | 2-methyl-piperidine | cyclohexyl | 4-fluoro | 2-methyl | Ex 7 (7) | >160 (d) | 435 (Cl) |
| 98 | N | 2-methyl-piperidine | 2-butylphenyl | 4-fluoro | 2,6-dimethyl | Ex 7 (30) | 168–170 (d) | 423 (Cl) |
| 99 | N | 2-methyl-piperidine | 2–propylphenyl | 4-fluoro | 2,6-dimethyl | Ex 7 (32) | 208–210 (d) | 409 (Cl) |
| 100 | CH | 2-methyl-piperidine | cyclohexyl | 4-fluoro | 2-methyl | Ex 4 (74) | >125 (d) | 434 (Cl) |
| 101 | N | 1-adamantine | cyclohexyl | 4-fluoro | 2-methyl | Ex 11 (24) | amorphous | 471 (EI) |
| 102 | N | 2-methyl-piperidine | cyclobutyl | 4-fluoro | 2,6-dimethyl | Ex 7 (12) | 136–138 | 420 (Cl) |
| 103 | N | 2-methyl-piperidine | cyclopropyl | 4-fluoro | 2,6-dimethyl | Ex 7 (20) | 219–220 | 406 (EI) |
| 104 | N | 1,2-tetrahydrooxazine | cyclopropyl | 4-fluoro | 2,6-dimethyl | Ex 5 (40) | 229–231 (d) | 395 (Cl) |
| 105 | N | 2-methyl-piperidine | cyclopropyl | 4-fluoro | 2-methyl | Ex 7 (18) | amorphous | 393 (Cl) |
| 106 | N | 1-methyl-cyclohexyl | cyclopropyl | 4-fluoro | 2-methyl | Ex 11 (63) | 205–207 | 391 (EI) |
| 107 | CH | 1,2-tetrahydrooxazine | cyclopropyl | 4-fluoro | 2-methyl | Ex 4 (70) | 140–142 (d) | 380 (Cl) |
| 108 | N | 2-methyl-piperidine | cyclopropyl | 4-methoxy | 2,6-dimethyl | Ex 5 (78) | 194–195 | 490 (Cl) |
| 109 | N | 2-methyl-piperidine | cycloproylmethyl | 4–fluoro | 2,6-dimethyl | Ex 7 (14) | amorphous | 420 (Cl) |
| 110 | CH | 1,2-tetrahydrooxazine[a] | cyclopropyl | 4-fluoro | H | Ex 4 (35) | 82–84 | 366 (Cl) |
| 111 | N | 2-methyl-piperidine | allyl | 4-fluoro | 2,6-dimethyl | Ex 7 (13) | amorphous | 406 (EI) |
| 112 | N | 2-methyl-piperidine | morpholinyl | 4-fluoro | 2,6-dimethyl | Ex 7 (3) | 169–171 | 453 (Cl) |
| 113 | N | 2-methyl-piperidine | 1-piperidinyl | 4-fluoro | 2,6-dimethyl | Ex 7 (3) | 170–172 | 451 (Cl) |
| 114 | N | 2-methyl-piperidine | 2-methyl-cyclopropyl | 4-fluoro | 2,6-dimethyl | Ex 5 (47) | 176–178 | 422 (Cl) |

KEY TO TABLE
[a]t-Butanol was used instead of 1,4-dioxane.
[b]Acetonitrile was used instead of 1,4-dioxane.
[c]Tetrahydrofuran (THF) was used instead of dimethylformamide (DMF).
[d]A 1:1 mixture of THF—DMF was used instead of DMF.
[e]A 2.5:1 mixture ot THF—DMF was used instead of DMF.
[f]Hydroiodide salt.
[g]Nitrate salt.
[h]EI = electron impact (M⁺); Cl = chemical ionization (M⁺ + 1); FAB = fast atom bombardment (M⁺ + 1).
[i]Yields reported are for the last step in the Example described. Unless otherwise noted, all compounds were isolated as hydrochloride salts.
[j]$[\alpha]^{25}_D = -179.3°$ (c = 1.0, MeOH).
[k]$[\alpha]^{25}_D = +180.1°$ (c = 1.0, MeOH).

We claim:
1. A compound of Formula (Ia):

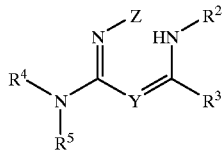

(Ia)

or a pharmaceutically acceptable salt thereof; wherein:
Y is CH;
Z is phenyl optionally substituted with from one to three substituents independently selected from the group consisting of $(C_1-C_6)$ alkyl; halo; hydroxy; $(C_1-C_6)$ alkoxy; amino; $(C_1-C_6)$ alkylamino; di$(C_1-C_6)$ alkylamino; and trifluoromethoxy;
$R^2$ is phenyl optionally substituted with from one to three substituents independently selected from the group consisting of $(C_1-C_6)$ alkyl; halo; hydroxy; $(C_1-C_6)$ alkoxy; amino; $(C_1-C_6)$ alkylamino; di$(C_1-C_6)$ alkylamino; —CF₃; —CN; —COR⁶; and —NHCOR⁶;
$R^3$ is phenyl optionally substituted with from one to three substituents independently selected from the group consisting of $(C_1-C6)$ alkyl; halo; hydroxy; $(C_1-C_6)$ alkoxy; amino; $(C_1-C_6)$ alkylamino; di$(C_1-C_6)$ alkylamino; and trifluoromethoxy;
$R^4$ and $R^5$ are independently $(C_1-C_{10})$ alkyl; or $R^4$ and $R^5$ are taken together with the nitrogen atom to which they are attached to form a (five to nine)-membered saturated heterocyclic ring in which one of the ring atoms may optionally be replaced with a heteroatom selected from the group consisting of nitrogen, oxygen and sulfur; wherein said (five to nine)-membered saturated heterocyclic ring may optionally be substituted with from one to three substituents independently selected from the group consisting of CR⁶; $(C_1-C_4)$ alkyl; oxo; and a ketal of the formula —$(CH_2)_m$—O—; with the proviso that said heterocycles may not be substituted next to a heteroatom by hydroxy or a ketal of the above formula;
$R^6$ is hydrogen; or $(C_1-C_6)$ alkyl; and
m is an integer of from one to three.
2. A compound according to claim 1, wherein Z is phenyl optionally substituted with from one to three substituents independently selected from the group consisting of $(C_1-C_6)$ alkyl, halo, hydroxy, $(C_1-C_6)$alkoxy, amino, $(C_{1-C6})$ alkylamino, di$(C_1-C_6)$-alkylamino and trifluoromethoxy.
3. A compound according to claim 2, wherein X is NR⁴R⁵ and R⁴ and R⁵ are taken together with the nitrogen atom to which they are attached to form an optionally substituted (five to nine)-membered saturated heterocyclic ring selected from piperidine, pyrrolidine, thiomorpholine, hexamethylenimine, morpholine, thiazolidine and 1,2-tetrahydrooxazine.

4. A compound according to claim 3, wherein X is an optionally substituted heterocycle selected from the group consisting of piperidine and 1,2-tetrahydrooxazine.

5. A compound according to claim 3, wherein $R^2$ is phenyl optionally substituted with halo, hydroxy or methoxy.

6. A compound according to claim 4, wherein $R^2$ is phenyl optionally substituted with halo, hydroxy or methoxy.

7. A compound according to claim 6, wherein $R^2$ is phenyl substituted in the 4-position of the phenyl ring with fluoro or methoxy.

8. A compound according to claim 3, wherein $R^3$ is phenyl substituted with two substituents independently selected from $(C_1-C_6)$alkyl, halo, hydroxy, $(C_1-C_6)$alkoxy, amino, $(C_1-C_6)$alkylamino, di$(C_1-C_6)$-alkylamino and trifluoroalkoxy.

9. A compound according to claim 4, wherein $R^3$ is phenyl substituted with two substituents independently selected from $(C_1-C_6)$alkyl, halo, hydroxy, $(C_1-C_6)$alkoxy, amino, $(C_1-C_6)$alkylamino, di$(C_1-C_6)$-alkylamino and trifluoroalkoxy.

10. A compound according to claim 6, wherein $R^3$ is phenyl substituted with two substituents independently selected from $(C_1-C_6)$alkyl, halo, hydroxy, $(C_1-C_6)$alkoxy, amino, $(C_1-C_6)$alkylamino di$(C_1-C_6)$-alkylamino and trifluoroalkoxy.

11. A compound according to claim 4 wherein said piperidine is substituted in the two position with $(C_1-C_4)$ alkyl.

12. A compound according to claim 8 wherein said piperidine is substituted in the two position with $(C_1-C_4)$ alkyl.

13. A compound according to claim 10 wherein said piperidine is substituted in the two position with $(C_1-C_4)$ alkyl.

14. A compound according to claim 11, wherein $R^3$ is 2,6-dimethylphenyl.

15. A compound according to claim 12, wherein $R^3$ is 2,6-dimethylphenyl.

16. A compound according to claim 13, wherein $R^3$ is 2,6-dimethylphenyl.

17. A pharmaceutical composition for treating a disease in a mammal, characterized by cholinergic deficient neurodegeneration, comprising a muscarinic receptor subtype M1 agonistic effective amount of a compound according to claim 1 or a pharmaceutically acceptable salt thereof and a pharmaceutically acceptable carrier.

18. A pharmaceutical composition for treating a disease according to claim 17 wherein said disease is Alzheimer's disease or age-related cognitive decline (ARCD).

19. A method of treating a disease in a mammal, characterized by cholinergic deficient neurodegeneration, comprising administering to said mammal a muscarinic receptor subtype M1 agonistic effective amount of a compound according to claim 1 or a pharmaceutically acceptable salt thereof.

20. A method of treating a disease according to claim 19, wherein said disease is Alzheimer's disease or age-related cognitive decline (ARCD).

* * * * *